US012746150B2

(12) United States Patent
Basciano et al.

(10) Patent No.: US 12,746,150 B2
(45) Date of Patent: Sep. 29, 2026

(54) THERMAL PAD WITH ENHANCED HEAT TRANSFER CHARACTERISTICS

(71) Applicant: C. R. Bard, Inc., Franklin Lakes, NJ (US)

(72) Inventors: Christopher A. Basciano, Apex, NC (US); Melody M. H. Kuroda, Durham, NC (US); Charles D. Shermer, Raleigh, NC (US)

(73) Assignee: C. R. Bard, Inc., Franklin Lakes, NJ (US)

(*) Notice: Subject to any disclaimer, the term of this patent is extended or adjusted under 35 U.S.C. 154(b) by 1054 days.

(21) Appl. No.: 17/837,956

(22) Filed: Jun. 10, 2022

(65) Prior Publication Data

US 2022/0401259 A1 Dec. 22, 2022

Related U.S. Application Data

(60) Provisional application No. 63/213,099, filed on Jun. 21, 2021.

(51) Int. Cl.
*A61F 7/02* (2006.01)
*A61F 7/00* (2006.01)

(52) U.S. Cl.
CPC ........ *A61F 7/02* (2013.01); *A61F 2007/0054* (2013.01); *A61F 2007/0247* (2013.01);
(Continued)

(58) Field of Classification Search
CPC ................ A61F 7/02; A61F 2007/0054; A61F 2007/0247; A61F 2007/0269;
(Continued)

(56) References Cited

U.S. PATENT DOCUMENTS 2,167,865 A 8/1939 Beecher
2,250,325 A 7/1941 Barnes
(Continued)

FOREIGN PATENT DOCUMENTS

AU 678753 B3 6/1997
AU 2007201161 B2 12/2010
(Continued)

OTHER PUBLICATIONS

PCT/US2022/013569 filed Jan. 24, 2022 International Search Report and Written Opinion dated Aug. 29, 2022.
(Continued)

*Primary Examiner* — Robert G Bachner
(74) *Attorney, Agent, or Firm* — Rutan & Tucker LLP

(57) ABSTRACT

Disclosed is a medical pad for exchanging thermal energy between a targeted temperature management (TTM) fluid and a patient. The pad includes a fluid channel extending between a fluid inlet and a fluid outlet, and a bottom channel wall that is disposed between the fluid and the patient during use of the pad. The wall is formed of a material having a thermal conductivity, and the wall includes elements embedded within the wall. The elements are formed of a material having a greater thermal conductivity than the wall material so that a composite thermal conductivity of the wall that is greater than the thermal conductivity of the wall material alone. The thermal energy exchange between the fluid and the patient is defined in accordance with the composite thermal conductivity. The pad can include channel shapes and features that enhance the heat transfer convection coefficient of the fluid within the channel.

20 Claims, 8 Drawing Sheets

(52) U.S. Cl.
CPC ................. *A61F 2007/0269* (2013.01); *A61F 2007/0273* (2013.01); *A61F 2007/0295* (2013.01)

(58) Field of Classification Search
CPC ...... A61F 2007/0273; A61F 2007/0295; A61F 2007/0246
See application file for complete search history.

(56) References Cited

U.S. PATENT DOCUMENTS

| | | | |
|---|---|---|---|
| 2,296,207 | A | 9/1942 | Kittinger |
| 2,595,328 | A | 5/1952 | Bowen |
| 2,602,302 | A | 7/1952 | Poux |
| 2,726,658 | A | 12/1955 | Chessey |
| 2,807,809 | A | 10/1957 | Kottemann |
| 3,075,529 | A | 1/1963 | Young, Jr. |
| 3,091,242 | A | 5/1963 | Johnson, Jr. et al. |
| 3,212,286 | A | 10/1965 | Curtis |
| 3,506,013 | A | 4/1970 | Zdenek |
| 3,734,293 | A | 5/1973 | Biskis |
| 3,830,676 | A | 8/1974 | Elkins |
| 3,867,939 | A | 2/1975 | Moore et al. |
| 3,900,035 | A | 8/1975 | Welch et al. |
| 3,927,671 | A | 12/1975 | Chittenden et al. |
| 3,945,617 | A | 3/1976 | Callery |
| 3,995,621 | A | 12/1976 | Fletcher et al. |
| 4,059,293 | A | 11/1977 | Sipler |
| 4,092,982 | A | 6/1978 | Salem |
| 4,108,146 | A | 8/1978 | Golden |
| 4,114,620 | A | 9/1978 | Moore et al. |
| 4,118,946 | A | 10/1978 | Tubin |
| 4,149,541 | A | 4/1979 | Gammons et al. |
| 4,154,245 | A | 5/1979 | Daily |
| 4,161,210 | A | 7/1979 | Reid et al. |
| 4,195,631 | A | 4/1980 | Baucom |
| 4,311,022 | A | 1/1982 | Hall |
| 4,444,727 | A | 4/1984 | Yanagihara et al. |
| 4,508,123 | A | 4/1985 | Wyatt et al. |
| 4,580,408 | A | 4/1986 | Stuebner |
| 4,753,241 | A | 6/1988 | Brannigan et al. |
| 4,834,705 | A | 5/1989 | Vaillancourt |
| 4,846,176 | A | 7/1989 | Golden |
| 4,867,748 | A | 9/1989 | Samuelsen |
| 4,884,304 | A | 12/1989 | Elkins |
| 4,886,063 | A | 12/1989 | Crews |
| 4,908,248 | A | 3/1990 | Nakashima et al. |
| 4,919,134 | A | 4/1990 | Streeter |
| 4,962,761 | A | 10/1990 | Golden |
| 4,971,056 | A | 11/1990 | Seacord |
| 4,981,135 | A | 1/1991 | Hardy |
| 4,989,607 | A | 2/1991 | Keusch et al. |
| 5,000,252 | A | 3/1991 | Faghri |
| 5,005,374 | A | 4/1991 | Spitler |
| 5,050,596 | A | 9/1991 | Walasek et al. |
| 5,062,414 | A | 11/1991 | Grim |
| 5,072,875 | A | 12/1991 | Zacoi |
| 5,090,409 | A | 2/1992 | Genis |
| 5,097,829 | A | 3/1992 | Quisenberry |
| 5,111,668 | A | 5/1992 | Parrish et al. |
| 5,113,666 | A | 5/1992 | Parrish et al. |
| 5,133,348 | A | 7/1992 | Mayn |
| 5,146,625 | A | 9/1992 | Steele et al. |
| 5,154,706 | A | 10/1992 | Cartmell et al. |
| 5,190,032 | A | 3/1993 | Zacoi |
| 5,265,669 | A | 11/1993 | Schneider |
| 5,268,022 | A | 12/1993 | Garrett et al. |
| 5,289,695 | A | 3/1994 | Parrish et al. |
| 5,300,103 | A | 4/1994 | Stempel et al. |
| 5,304,213 | A | 4/1994 | Berke et al. |
| 5,304,216 | A | 4/1994 | Wallace |
| 5,320,164 | A | 6/1994 | Szczesuil et al. |
| 5,329,638 | A | 7/1994 | Hansen et al. |
| 5,383,919 | A | 1/1995 | Kelly et al. |
| 5,393,462 | A | 2/1995 | Avery |
| 5,405,366 | A | 4/1995 | Fox et al. |
| 5,407,421 | A | 4/1995 | Goldsmith |
| 5,409,500 | A | 4/1995 | Dyrek |
| 5,411,541 | A | 5/1995 | Bell et al. |
| 5,423,751 | A | 6/1995 | Harrison et al. |
| 5,431,622 | A | 7/1995 | Pyrozyk et al. |
| 5,437,673 | A | 8/1995 | Baust et al. |
| 5,456,701 | A | 10/1995 | Stout |
| 5,466,250 | A | 11/1995 | Johnson, Jr. et al. |
| 5,470,353 | A | 11/1995 | Jensen |
| 5,476,489 | A | 12/1995 | Koewler |
| 5,484,448 | A | 1/1996 | Steele et al. |
| 5,486,207 | A | 1/1996 | Mahawili |
| 5,514,169 | A | 5/1996 | Dickerhoff et al. |
| 5,545,194 | A | 8/1996 | Augustine |
| 5,566,413 | A | 10/1996 | Webb et al. |
| 5,605,144 | A | 2/1997 | Simmons et al. |
| 5,609,620 | A | 3/1997 | Daily |
| 5,620,482 | A | 4/1997 | Augustine et al. |
| 5,624,477 | A | 4/1997 | Armond |
| 5,634,940 | A | 6/1997 | Panyard |
| 5,640,728 | A | 6/1997 | Graebe |
| 5,645,855 | A | 7/1997 | Lorenz |
| 5,658,325 | A | 8/1997 | Augustine |
| 5,662,695 | A | 9/1997 | Mason et al. |
| 5,683,439 | A | 11/1997 | Jensen |
| 5,720,774 | A | 2/1998 | Glucksman |
| 5,733,318 | A | 3/1998 | Augustine |
| 5,755,755 | A | 5/1998 | Panyard |
| 5,785,716 | A | 7/1998 | Bayron et al. |
| 5,806,335 | A | 9/1998 | Herbert et al. |
| 5,824,025 | A | 10/1998 | Augustine |
| 5,837,002 | A | 11/1998 | Augustine et al. |
| 5,840,080 | A | 11/1998 | Der Ovanesian |
| 5,843,145 | A | 12/1998 | Brink |
| 5,871,526 | A | 2/1999 | Gibbs et al. |
| 5,879,378 | A | 3/1999 | Usui |
| 5,887,437 | A | 3/1999 | Maxim |
| 5,913,849 | A | 6/1999 | Sundstrom et al. |
| 5,947,914 | A | 9/1999 | Augustine |
| 5,948,012 | A | 9/1999 | Mahaffey et al. |
| 5,968,000 | A | 10/1999 | Harrison et al. |
| 5,986,163 | A | 11/1999 | Augustine |
| 5,989,285 | A | 11/1999 | DeVilbiss et al. |
| 6,010,528 | A | 1/2000 | Augustine et al. |
| 6,019,783 | A | 2/2000 | Philips et al. |
| 6,030,412 | A | 2/2000 | Klatz et al. |
| 6,047,106 | A | 4/2000 | Salyer |
| 6,074,415 | A | 6/2000 | Der Ovanesian |
| 6,083,256 | A | 7/2000 | Der Ovanesian |
| 6,083,418 | A | 7/2000 | Czarnecki et al. |
| 6,117,164 | A | 9/2000 | Gildersleeve et al. |
| 6,176,869 | B1 | 1/2001 | Mason et al. |
| 6,176,870 | B1 | 1/2001 | Augustine |
| 6,185,744 | B1 | 2/2001 | Poholski |
| 6,188,930 | B1 | 2/2001 | Carson |
| 6,189,149 | B1 | 2/2001 | Allen |
| 6,189,550 | B1 | 2/2001 | Stickel et al. |
| 6,197,045 | B1 | 3/2001 | Carson |
| 6,234,538 | B1 | 5/2001 | Lauer |
| 6,238,427 | B1 | 5/2001 | Matta |
| 6,255,552 | B1 | 7/2001 | Cummings et al. |
| 6,257,011 | B1 | 7/2001 | Siman-Tov et al. |
| 6,290,716 | B1 | 9/2001 | Augustine |
| 6,336,935 | B1 | 1/2002 | Davis et al. |
| 6,349,560 | B1 | 2/2002 | Maier-Laxhuber et al. |
| 6,352,550 | B1 | 3/2002 | Gildersleeve et al. |
| 6,364,937 | B1 | 4/2002 | McMahon |
| 6,371,976 | B1 | 4/2002 | Vzalik et al. |
| 6,375,674 | B1 | 4/2002 | Carson |
| 6,389,839 | B1 | 5/2002 | Sabin |
| 6,436,130 | B1 | 8/2002 | Philips et al. |
| 6,451,036 | B1 | 9/2002 | Heitzmann et al. |
| 6,454,792 | B1 | 9/2002 | Noda et al. |
| 6,461,379 | B1 | 10/2002 | Carson et al. |
| 6,463,212 | B1 | 10/2002 | Salyer |
| 6,503,297 | B1 | 1/2003 | Lu et al. |
| 6,508,831 | B1 | 1/2003 | Kushnir |
| 6,508,859 | B1 | 1/2003 | Zia et al. |

(56) References Cited

U.S. PATENT DOCUMENTS

| | | | |
|---|---|---|---|
| 6,511,501 | B1 | 1/2003 | Augustine et al. |
| 6,511,502 | B2 | 1/2003 | Fletcher |
| 6,517,510 | B1 | 2/2003 | Stewart et al. |
| D471,987 | S | 3/2003 | Hoglund et al. |
| D472,322 | S | 3/2003 | Hoglund et al. |
| 6,551,348 | B1 | 4/2003 | Blalock et al. |
| D474,544 | S | 5/2003 | Hoglund et al. |
| 6,559,096 | B1 | 5/2003 | Smith et al. |
| 6,584,797 | B1 | 7/2003 | Smith et al. |
| 6,589,270 | B2 | 7/2003 | Augustine |
| 6,591,630 | B2 | 7/2003 | Smith et al. |
| 6,601,404 | B1 | 8/2003 | Roderick |
| 6,613,030 | B1 | 9/2003 | Coles et al. |
| 6,620,187 | B2 | 9/2003 | Carson et al. |
| 6,620,188 | B1 | 9/2003 | Ginsburg et al. |
| 6,645,232 | B2 | 11/2003 | Carson |
| 6,648,905 | B2 | 11/2003 | Hoglund et al. |
| 6,653,607 | B2 | 11/2003 | Ellis et al. |
| D483,125 | S | 12/2003 | Hoglund et al. |
| 6,660,027 | B2 | 12/2003 | Gruszecki et al. |
| 6,669,715 | B2 | 12/2003 | Hoglund et al. |
| 6,682,525 | B2 | 1/2004 | Lalonde et al. |
| D487,147 | S | 2/2004 | Ellingboe et al. |
| D487,148 | S | 2/2004 | Ellingboe et al. |
| 6,688,132 | B2 | 2/2004 | Smith et al. |
| 6,692,518 | B2 | 2/2004 | Carson |
| 6,699,267 | B2 | 3/2004 | Voorhees et al. |
| 6,701,724 | B2 | 3/2004 | Smith et al. |
| 6,743,250 | B2 | 6/2004 | Renfro |
| 6,755,801 | B2 | 6/2004 | Utterberg et al. |
| 6,755,852 | B2 | 6/2004 | Lachenbruch et al. |
| D492,773 | S | 7/2004 | Ellingboe et al. |
| 6,770,848 | B2 | 8/2004 | Haas et al. |
| 6,799,063 | B2 | 9/2004 | Carson |
| 6,800,087 | B2 | 10/2004 | Papay et al. |
| 6,802,855 | B2 | 10/2004 | Ellingboe et al. |
| 6,802,885 | B2 | 10/2004 | Luk et al. |
| 6,818,012 | B2 | 11/2004 | Ellingboe |
| 6,827,728 | B2 | 12/2004 | Ellingboe et al. |
| 6,846,322 | B2 | 1/2005 | Kane et al. |
| 6,858,068 | B2 | 2/2005 | Smith et al. |
| 6,878,156 | B1 | 4/2005 | Noda |
| 6,893,453 | B2 | 5/2005 | Agarwal et al. |
| 6,904,956 | B2 | 6/2005 | Noel |
| 6,909,074 | B1 | 6/2005 | Bradley |
| 6,921,198 | B2 | 7/2005 | Gruszecki et al. |
| 6,931,875 | B1 | 8/2005 | Allen et al. |
| 6,942,644 | B2 | 9/2005 | Worthen |
| 6,960,243 | B1 | 11/2005 | Smith et al. |
| 6,968,711 | B2 | 11/2005 | Smith et al. |
| 6,969,399 | B2 | 11/2005 | Schock et al. |
| 7,008,445 | B2 | 3/2006 | Lennox |
| 7,022,099 | B2 | 4/2006 | Litzie et al. |
| 7,044,960 | B2 | 5/2006 | Voorhees et al. |
| 7,052,509 | B2 | 5/2006 | Lennox et al. |
| 7,055,575 | B2 | 6/2006 | Noel |
| 7,056,335 | B2 | 6/2006 | Agarwal et al. |
| 7,063,718 | B2 | 6/2006 | Dobak, III |
| 7,077,858 | B2 | 7/2006 | Fletcher et al. |
| 7,097,657 | B2 | 8/2006 | Noda et al. |
| 7,101,389 | B1 | 9/2006 | Augustine et al. |
| 7,122,047 | B2 | 10/2006 | Grahn et al. |
| 7,160,316 | B2 | 1/2007 | Hamilton et al. |
| 7,172,586 | B1 | 2/2007 | Dae et al. |
| 7,240,720 | B2 | 7/2007 | Noel |
| 7,303,554 | B2 | 12/2007 | Lalonde et al. |
| 7,303,579 | B2 | 12/2007 | Schock et al. |
| 7,338,516 | B2 | 3/2008 | Quincy, III et al. |
| 7,361,186 | B2 | 4/2008 | Voorhees et al. |
| 7,377,935 | B2 | 5/2008 | Schock et al. |
| 7,507,250 | B2 | 3/2009 | Lennox |
| 7,517,360 | B2 | 4/2009 | Frey et al. |
| RE40,815 | E | 6/2009 | Kudaravalli et al. |
| 7,547,320 | B2 | 6/2009 | Schook et al. |
| RE40,868 | E | 8/2009 | Ryba et al. |
| 7,621,944 | B2 | 11/2009 | Wilson et al. |
| 7,621,945 | B2 | 11/2009 | Lennox et al. |
| 7,666,213 | B2 | 2/2010 | Freedman, Jr. et al. |
| 7,678,716 | B2 | 3/2010 | Yahiaoui et al. |
| 7,686,840 | B2 | 3/2010 | Quincy, III et al. |
| 7,727,228 | B2 | 6/2010 | Abboud et al. |
| 7,731,739 | B2 | 6/2010 | Schock et al. |
| 7,744,640 | B1 | 6/2010 | Faries, Jr. et al. |
| 7,749,261 | B2 | 7/2010 | Hansen et al. |
| 7,763,061 | B2 | 7/2010 | Schorr et al. |
| 7,771,461 | B2 | 8/2010 | Schock et al. |
| 7,784,304 | B2 | 8/2010 | Trinh et al. |
| 7,799,063 | B2 | 9/2010 | Ingram et al. |
| 7,827,815 | B2 | 11/2010 | Carson et al. |
| 7,867,266 | B2 | 1/2011 | Collins |
| 7,892,269 | B2 | 2/2011 | Collins et al. |
| 7,896,910 | B2 | 3/2011 | Schirrmacher et al. |
| 7,918,243 | B2 | 4/2011 | Diodati et al. |
| 8,047,010 | B2 | 11/2011 | Carson et al. |
| 8,052,624 | B2 | 11/2011 | Buchanan et al. |
| 8,066,752 | B2 | 11/2011 | Hamilton et al. |
| 8,182,521 | B2 | 5/2012 | Kane et al. |
| 8,187,697 | B2 | 5/2012 | Quincy, III et al. |
| 8,216,163 | B2 | 7/2012 | Edelman |
| 8,283,602 | B2 | 10/2012 | Augustine et al. |
| 8,454,671 | B2 | 6/2013 | Lennox et al. |
| D685,916 | S | 7/2013 | Hoglund |
| 8,491,644 | B1 | 7/2013 | Carson et al. |
| 8,597,217 | B2 | 12/2013 | Lowe et al. |
| 8,597,339 | B2 | 12/2013 | Augustine et al. |
| 8,603,150 | B2 | 12/2013 | Kane et al. |
| 8,632,576 | B2 | 1/2014 | Quisenberry |
| 8,647,374 | B2 | 2/2014 | Koewler |
| 8,715,330 | B2 | 5/2014 | Lowe et al. |
| 8,778,119 | B2 | 7/2014 | Starr et al. |
| 8,808,344 | B2 | 8/2014 | Scott et al. |
| 8,840,581 | B2 | 9/2014 | McGill et al. |
| 9,034,458 | B2 | 5/2015 | Li |
| 9,078,742 | B2 | 7/2015 | Quincy, III et al. |
| 9,089,462 | B1 | 7/2015 | Lafleche |
| 9,211,358 | B2 | 12/2015 | Sinko et al. |
| 9,278,024 | B2 | 3/2016 | Scott et al. |
| 9,333,112 | B2 | 5/2016 | Carson |
| 9,433,527 | B2 | 9/2016 | Varga et al. |
| 9,552,706 | B2 | 1/2017 | Schneider et al. |
| 9,566,185 | B2 | 2/2017 | Carson et al. |
| 9,622,907 | B2 | 4/2017 | Carson et al. |
| 9,642,404 | B2 | 5/2017 | Giles et al. |
| 9,687,386 | B2 | 6/2017 | Carson |
| 9,763,823 | B2 | 9/2017 | Voorhees et al. |
| 9,907,889 | B2 | 3/2018 | Locke et al. |
| 10,010,452 | B2 | 7/2018 | Wenske et al. |
| 10,123,902 | B2 | 11/2018 | Carson et al. |
| 10,220,198 | B2 | 3/2019 | Fuchs et al. |
| 10,258,501 | B2 | 4/2019 | Carson |
| 10,376,412 | B2 | 8/2019 | Brienza et al. |
| 10,441,458 | B2 | 10/2019 | Voorhees et al. |
| 10,441,707 | B2 | 10/2019 | Voorhees et al. |
| 10,548,778 | B2 | 2/2020 | Hassenpflug et al. |
| 10,610,424 | B1 | 4/2020 | Hoover |
| D887,426 | S | 6/2020 | Matsushita |
| 10,912,672 | B1 | 2/2021 | Jones et al. |
| D922,424 | S | 6/2021 | Frueh et al. |
| D925,574 | S | 7/2021 | Beko |
| D928,188 | S | 8/2021 | Giannino et al. |
| 11,173,071 | B1 | 11/2021 | Tawil et al. |
| D939,550 | S | 12/2021 | Miyai et al. |
| 11,234,859 | B2 | 2/2022 | Voorhees et al. |
| D947,216 | S | 3/2022 | Leininger |
| 11,285,039 | B2 | 3/2022 | Steele et al. |
| D948,534 | S | 4/2022 | Bessette et al. |
| D952,666 | S | 5/2022 | Sajan |
| D959,475 | S | 8/2022 | Norman |
| D960,191 | S | 8/2022 | Feit et al. |
| D973,067 | S | 12/2022 | Oh et al. |
| 11,975,123 | B2 | 5/2024 | Appel et al. |
| 2001/0034545 | A1 | 10/2001 | Elkins |
| 2001/0039439 | A1 | 11/2001 | Elkins et al. |
| 2002/0007203 | A1 | 1/2002 | Gilmartin et al. |

(56) References Cited

U.S. PATENT DOCUMENTS

2002/0015689 A1 2/2002 Munro et al.
2002/0107558 A1 8/2002 Clifton et al.
2002/0111657 A1 8/2002 Dae et al.
2002/0138121 A1 9/2002 Fox
2002/0161419 A1 10/2002 Carson et al.
2003/0074038 A1 4/2003 Gruszecki et al.
2003/0078638 A1 4/2003 Voorhees et al.
2003/0078639 A1 4/2003 Carson
2003/0078640 A1 4/2003 Carson et al.
2003/0109911 A1 6/2003 Lachenbruch et al.
2003/0114903 A1 6/2003 Ellingboe
2003/0135252 A1 7/2003 MacHold et al.
2003/0149359 A1 8/2003 Smith
2003/0149461 A1 8/2003 Johnson
2003/0150232 A1 8/2003 Brudnicki
2003/0163179 A1 8/2003 Hoglund et al.
2003/0163180 A1 8/2003 Hoglund et al.
2003/0163183 A1 8/2003 Carson
2003/0163185 A1 8/2003 Carson
2003/0212416 A1 11/2003 Cinelli et al.
2004/0030372 A1 2/2004 Ellingboe et al.
2004/0030373 A1 2/2004 Ellingboe et al.
2004/0059212 A1 3/2004 Abreu
2004/0064170 A1 4/2004 Radons et al.
2004/0064171 A1 4/2004 Briscoe et al.
2004/0073280 A1 4/2004 Dae et al.
2004/0082886 A1 4/2004 Timpson
2004/0087606 A1 5/2004 Voorhees et al.
2004/0133253 A1 7/2004 Grahn et al.
2004/0158303 A1 8/2004 Lennox et al.
2004/0225341 A1 11/2004 Schock et al.
2004/0243122 A1 12/2004 Auth et al.
2004/0252750 A1 12/2004 Gruszecki et al.
2004/0255362 A1 12/2004 Soerens et al.
2004/0260369 A1 12/2004 Schock et al.
2004/0267339 A1 12/2004 Yon et al.
2005/0028551 A1 2/2005 Noda et al.
2005/0060012 A1 3/2005 Voorhees et al.
2005/0065583 A1 3/2005 Voorhees et al.
2005/0096714 A1 5/2005 Freedman et al.
2005/0177212 A1 8/2005 Njemanze
2005/0187502 A1 8/2005 Krempel et al.
2005/0244629 A1 11/2005 Usui et al.
2005/0288749 A1 12/2005 Lachenbruch
2006/0024053 A1 2/2006 Grant
2006/0030916 A1 2/2006 Lennox
2006/0036304 A1 2/2006 Cordani et al.
2006/0058858 A1 3/2006 Smith
2006/0069418 A1 3/2006 Schock et al.
2006/0074469 A1 4/2006 Lennox et al.
2006/0122673 A1 6/2006 Callister et al.
2006/0124141 A1 6/2006 Dobak
2006/0136023 A1 6/2006 Dobak
2006/0161232 A1 7/2006 Kasza et al.
2006/0190066 A1 8/2006 Worthen
2006/0235114 A1 10/2006 Kitazono et al.
2006/0247744 A1 11/2006 Nest et al.
2006/0276089 A1 12/2006 Amarasinghe et al.
2006/0287697 A1 12/2006 Lennox
2006/0293734 A1 12/2006 Scott et al.
2007/0016270 A1* 1/2007 Stelea ........................ A61F 7/10 607/96
2007/0043409 A1 2/2007 Brian et al.
2007/0049997 A1 3/2007 Fields et al.
2007/0054122 A1 3/2007 Paisner et al.
2007/0068931 A1 3/2007 Augustine et al.
2007/0073368 A1 3/2007 Cazzini et al.
2007/0100404 A1 5/2007 Ko et al.
2007/0173735 A1 7/2007 Callister et al.
2007/0213793 A1 9/2007 Hayes
2007/0225782 A1 9/2007 Taylor
2007/0244475 A1 10/2007 Carson et al.
2007/0270925 A1 11/2007 Levinson
2008/0027523 A1 1/2008 Behringer et al.
2008/0046046 A1 2/2008 Ginsburg
2008/0114431 A1 5/2008 Ginsburg
2008/0147152 A1 6/2008 Quincy et al.
2008/0249524 A1 10/2008 Dunning
2008/0255644 A1 10/2008 Carson
2008/0269852 A1 10/2008 Lennox et al.
2008/0275534 A1 11/2008 Noel
2009/0018504 A1 1/2009 Pile-Spellman et al.
2009/0043366 A1 2/2009 Dae
2009/0066079 A1 3/2009 Miros et al.
2009/0088825 A1 4/2009 Ota
2009/0099629 A1 4/2009 Carson et al.
2009/0131835 A1 5/2009 Voorhees et al.
2009/0149925 A1 6/2009 MacDonald et al.
2009/0157000 A1 6/2009 Waller
2009/0177184 A1 7/2009 Christensen et al.
2009/0182400 A1 7/2009 Dae et al.
2009/0228082 A1 9/2009 Ross et al.
2009/0250367 A1 10/2009 Murdoch et al.
2009/0280182 A1 11/2009 Beck et al.
2009/0287283 A1 11/2009 Biser et al.
2009/0299287 A1 12/2009 Carson et al.
2009/0312823 A1 12/2009 Patience et al.
2009/0326619 A1 12/2009 Kagan
2010/0016933 A1 1/2010 Chen et al.
2010/0137951 A1 6/2010 Lennox et al.
2010/0168825 A1 7/2010 Barbknecht
2010/0198122 A1 8/2010 Freund
2010/0198320 A1 8/2010 Pierre et al.
2010/0204765 A1 8/2010 Hall et al.
2010/0217260 A1 8/2010 Aramayo
2010/0241073 A1 9/2010 Andersen et al.
2010/0312160 A1 12/2010 Creighton et al.
2010/0312202 A1 12/2010 Henley et al.
2011/0021960 A1 1/2011 Filtvedt et al.
2011/0029051 A1 2/2011 Ross
2011/0045056 A1 2/2011 Munro et al.
2011/0125238 A1 5/2011 Nofzinger
2011/0152982 A1 6/2011 Richardson
2011/0166633 A1 7/2011 Stull
2011/0172749 A1 7/2011 Christensen et al.
2011/0172750 A1 7/2011 Cassidy et al.
2011/0306972 A1 12/2011 Widenhouse et al.
2011/0307040 A1 12/2011 Peterson
2011/0308781 A1 12/2011 O'Riordan et al.
2011/0313497 A1 12/2011 Mcfarlane
2012/0046720 A1 2/2012 Ishizaki
2012/0065715 A1 3/2012 Carson
2012/0080031 A1 4/2012 Belson
2012/0095536 A1 4/2012 Machold et al.
2012/0172774 A1 7/2012 Lowe et al.
2012/0185021 A1 7/2012 Johnson et al.
2012/0191035 A1 7/2012 Stephan
2012/0204881 A1 8/2012 Davidson et al.
2012/0220960 A1 8/2012 Ruland
2012/0288848 A1 11/2012 Latham et al.
2013/0023808 A1 1/2013 Brown et al.
2013/0116760 A1 5/2013 Carson et al.
2013/0138185 A1 5/2013 Paxman et al.
2013/0190667 A1 7/2013 Kane et al.
2013/0238042 A1 9/2013 Gildersleeve et al.
2013/0238043 A1 9/2013 Beardall et al.
2013/0310725 A1 11/2013 Jerrells et al.
2014/0039451 A1 2/2014 Bangera et al.
2014/0046411 A1 2/2014 Elkins et al.
2014/0172050 A1 6/2014 Dabrowiak
2014/0214138 A1* 7/2014 Voorhees .................. A61F 7/10 607/104
2014/0222121 A1 8/2014 Spence et al.
2014/0228717 A1 8/2014 Parish et al.
2014/0228918 A1 8/2014 Brienza et al.
2014/0276253 A1 9/2014 Varga et al.
2014/0277301 A1 9/2014 Varga et al.
2014/0288621 A1 9/2014 Efremkin
2014/0316494 A1 10/2014 Augustine et al.
2014/0343639 A1 11/2014 Hopper et al.
2015/0025606 A1 1/2015 Davis
2015/0051673 A1 2/2015 Rivas Tapia
2015/0119963 A1 4/2015 Cosse
2015/0173942 A1 6/2015 Whitely

(56) References Cited

U.S. PATENT DOCUMENTS

| | | | |
|---|---|---|---|
| 2015/0209174 | A1 | 7/2015 | Abreu |
| 2015/0209192 | A1 | 7/2015 | Manion et al. |
| 2015/0223972 | A1 | 8/2015 | Dabrowiak |
| 2015/0230973 | A1 | 8/2015 | Dabrowiak et al. |
| 2015/0231009 | A1 | 8/2015 | Lewis |
| 2015/0250643 | A1 | 9/2015 | Paradis |
| 2015/0290042 | A1 | 10/2015 | Freer et al. |
| 2015/0366703 | A1 | 12/2015 | Du |
| 2015/0373781 | A1 | 12/2015 | Augustine et al. |
| 2015/0374045 | A1 | 12/2015 | Codner et al. |
| 2016/0008166 | A1 | 1/2016 | Voorhees et al. |
| 2016/0022477 | A1 | 1/2016 | Schaefer et al. |
| 2016/0038336 | A1 | 2/2016 | Hilton et al. |
| 2016/0310316 | A1 | 10/2016 | Hixson, Jr. |
| 2016/0324683 | A1 | 11/2016 | Carson |
| 2017/0049618 | A1 | 2/2017 | Ward et al. |
| 2017/0135855 | A1 | 5/2017 | Stefan et al. |
| 2017/0151087 | A1 | 6/2017 | Carson et al. |
| 2017/0189225 | A1 | 7/2017 | Voorhees et al. |
| 2017/0209305 | A1 | 7/2017 | Kaforey et al. |
| 2017/0224528 | A1 | 8/2017 | Berg et al. |
| 2017/0246029 | A1 | 8/2017 | Clark |
| 2017/0246031 | A1 | 8/2017 | Benyaminpour et al. |
| 2017/0246374 | A1 | 8/2017 | Voorhees et al. |
| 2017/0348144 | A1 | 12/2017 | Taylor et al. |
| 2017/0348145 | A1 | 12/2017 | Voorhees et al. |
| 2017/0354534 | A1 | 12/2017 | Paradis et al. |
| 2018/0000255 | A1 | 1/2018 | Youngblood et al. |
| 2018/0014967 | A1 | 1/2018 | Taylor |
| 2018/0042762 | A1 | 2/2018 | Galer |
| 2018/0042763 | A1 | 2/2018 | Galer et al. |
| 2018/0064594 | A1 | 3/2018 | Finch, Jr. et al. |
| 2018/0140407 | A1 | 5/2018 | Yoskowitz |
| 2018/0207024 | A1 | 7/2018 | Dabrowiak et al. |
| 2018/0214297 | A1 | 8/2018 | Hughett et al. |
| 2018/0214302 | A1 | 8/2018 | Dabrowiak et al. |
| 2018/0263677 | A1 | 9/2018 | Hilton et al. |
| 2018/0263748 | A1 | 9/2018 | Quinn |
| 2018/0295980 | A1 | 10/2018 | Boersma et al. |
| 2018/0376539 | A1 | 12/2018 | Augustine et al. |
| 2019/0083322 | A1 | 3/2019 | Huang et al. |
| 2019/0085644 | A1 | 3/2019 | Ames et al. |
| 2019/0099288 | A1 | 4/2019 | Vergara et al. |
| 2019/0117446 | A1 | 4/2019 | Carson et al. |
| 2019/0192337 | A1 | 6/2019 | Taylor et al. |
| 2019/0201574 | A1 | 7/2019 | Delury et al. |
| 2019/0262169 | A1* | 8/2019 | Vergara ................. A61F 7/0053 |
| 2019/0331277 | A1 | 10/2019 | Vachon |
| 2020/0001022 | A1 | 1/2020 | Landy, III et al. |
| 2020/0071051 | A1 | 3/2020 | Lewis |
| 2020/0129326 | A1 | 4/2020 | Sinha et al. |
| 2020/0155341 | A1 | 5/2020 | Voorhees et al. |
| 2020/0214471 | A1 | 7/2020 | Paperno |
| 2020/0246180 | A1 | 8/2020 | Liang et al. |
| 2020/0345971 | A1 | 11/2020 | Schirm et al. |
| 2020/0405530 | A1 | 12/2020 | Taylor et al. |
| 2021/0060230 | A1 | 3/2021 | Hopper et al. |
| 2021/0123641 | A1 | 4/2021 | Monazami et al. |
| 2022/0087874 | A1 | 3/2022 | Schneider et al. |
| 2022/0151821 | A1 | 5/2022 | Voorhees et al. |
| 2022/0192865 | A1 | 6/2022 | Hughett, Sr. et al. |
| 2022/0192867 | A1 | 6/2022 | Stich et al. |
| 2022/0233344 | A1 | 7/2022 | Hoglund |
| 2022/0233347 | A1 | 7/2022 | Canary et al. |
| 2022/0265468 | A1 | 8/2022 | Xu et al. |
| 2022/0280336 | A1 | 9/2022 | Smith et al. |
| 2022/0287875 | A1 | 9/2022 | Minchew et al. |
| 2022/0287876 | A1 | 9/2022 | Smith et al. |
| 2022/0296413 | A1 | 9/2022 | Jones |
| 2022/0296414 | A1 | 9/2022 | Bible et al. |
| 2022/0304847 | A1 | 9/2022 | Kuroda et al. |
| 2022/0313478 | A1 | 10/2022 | Johnston |
| 2022/0347009 | A1 | 11/2022 | Hughett, Sr. et al. |
| 2022/0406017 | A1 | 12/2022 | Wang et al. |
| 2023/0000668 | A1 | 1/2023 | Walker et al. |
| 2023/0009524 | A1 | 1/2023 | Johnston et al. |
| 2023/0011631 | A1 | 1/2023 | Yin et al. |
| 2023/0019048 | A1 | 1/2023 | Stich et al. |
| 2023/0021245 | A1 | 1/2023 | Walker et al. |
| 2023/0040583 | A1 | 2/2023 | Falis et al. |
| 2023/0077318 | A9 | 3/2023 | Voorhees et al. |
| 2023/0190519 | A1 | 6/2023 | Stich et al. |
| 2024/0065884 | A1 | 2/2024 | Fallows et al. |
| 2024/0082052 | A1 | 3/2024 | Cho et al. |
| 2024/0091054 | A1 | 3/2024 | Boone-Worthman et al. |
| 2024/0099878 | A1 | 3/2024 | Voorhees et al. |
| 2024/0108497 | A1 | 4/2024 | Daw et al. |
| 2024/0366422 | A1 | 11/2024 | Johnston et al. |
| 2025/0032310 | A1 | 1/2025 | Stich et al. |
| 2025/0041107 | A1 | 2/2025 | Walker et al. |
| 2025/0110628 | A1 | 4/2025 | Litman et al. |
| 2025/0134705 | A1 | 5/2025 | Stich et al. |
| 2025/0143918 | A1 | 5/2025 | Voorhees et al. |
| 2025/0161107 | A1 | 5/2025 | Stich et al. |
| 2025/0198550 | A1 | 6/2025 | Johnston et al. |
| 2025/0332025 | A1 | 10/2025 | Brooks et al. |
| 2026/0026965 | A1 | 1/2026 | Xu et al. |
| 2026/0102279 | A1 | 4/2026 | Canary et al. |

FOREIGN PATENT DOCUMENTS

| | | | |
|---|---|---|---|
| CA | 2729122 | A1 | 7/2002 |
| CA | 2193385 | C | 9/2006 |
| CN | 102026596 | A | 4/2011 |
| CN | 101389372 | B | 8/2012 |
| CN | 102746518 | A | 10/2012 |
| CN | 103939695 | B | 3/2016 |
| CN | 305928532 | | 7/2020 |
| CN | 111643265 | A | 9/2020 |
| CN | 306402573 | | 3/2021 |
| CN | 113230017 | A | 8/2021 |
| CN | 307690236 | | 11/2022 |
| CN | 309180016 | | 3/2025 |
| DE | 102014118510 | A1 | 6/2016 |
| EP | 0862901 | A1 | 9/1998 |
| EP | 1073388 | A1 | 2/2001 |
| EP | 1616543 | A2 | 1/2006 |
| EP | 1641503 | A2 | 4/2006 |
| EP | 1718894 | B1 | 7/2010 |
| EP | 2204150 | A1 | 7/2010 |
| EP | 2269546 | A1 | 1/2011 |
| GB | 2118440 | A | 11/1983 |
| JP | H09508045 | A | 8/1997 |
| JP | 2002-534160 | A | 10/2002 |
| JP | 2007029638 | A | 2/2007 |
| JP | 2013248293 | A | 12/2013 |
| KR | 20110020420 | A | 3/2011 |
| WO | 9807397 | A1 | 2/1998 |
| WO | 98/31310 | A1 | 7/1998 |
| WO | 199944552 | A1 | 9/1999 |
| WO | 9953874 | A1 | 10/1999 |
| WO | 2000040185 | A1 | 7/2000 |
| WO | 2003086253 | A2 | 10/2003 |
| WO | 2004075949 | A2 | 9/2004 |
| WO | 2005028984 | A1 | 3/2005 |
| WO | 2005117546 | A2 | 12/2005 |
| WO | 2007120677 | A2 | 10/2007 |
| WO | 2009/090403 | A1 | 7/2009 |
| WO | 2009147413 | A1 | 12/2009 |
| WO | 2009148636 | A1 | 12/2009 |
| WO | 2012125916 | A2 | 9/2012 |
| WO | 2012138980 | A2 | 10/2012 |
| WO | 2015084925 | A1 | 6/2015 |
| WO | 2016057119 | A1 | 4/2016 |
| WO | 2016123500 | A1 | 8/2016 |
| WO | 2017/127768 | A1 | 7/2017 |
| WO | 2018075576 | A1 | 4/2018 |
| WO | 2022/159879 | A1 | 7/2022 |
| WO | 2022155130 | A1 | 7/2022 |
| WO | 2022155132 | A1 | 7/2022 |
| WO | 2022159513 | A1 | 7/2022 |
| WO | 2022/165068 | A1 | 8/2022 |
| WO | 2022235513 | A1 | 11/2022 |
| WO | 2023121674 | A1 | 6/2023 |

(56) References Cited

FOREIGN PATENT DOCUMENTS

| | | | |
|---|---|---|---|
| WO | 2023140870 | A1 | 7/2023 |
| WO | 2023154050 | A1 | 8/2023 |
| WO | 2023229609 | A1 | 11/2023 |

OTHER PUBLICATIONS

PCT/US2022/016020 filed Feb. 10, 2022 International Search Report and Written Opinion dated Oct. 31, 2022.
U.S. Appl. No. 17/547,128, filed Dec. 9, 2021 Restriction Requirement dated Sep. 5, 2024.
U.S. Appl. No. 17/583,090, filed Jan. 24, 2022 Restriction Requirement dated Sep. 6, 2024.
U.S. Appl. No. 17/686,301, filed Mar. 3, 2022 Non-Final Office Action dated Oct. 1, 2024.
U.S. Appl. No. 17/689,791, filed Mar. 8, 2022 Restriction Requirement dated Oct. 16, 2024.
U.S. Appl. No. 17/691,990, filed Mar. 10, 2022 Restriction Requirement dated Oct. 16, 2024.
U.S. Appl. No. 17/709,019, filed Mar. 30, 2022 Restriction Requirement dated Oct. 16, 2024.
U.S. Appl. No. 17/723,210, filed Apr. 18, 2022 Restriction Requirement dated Oct. 16, 2024.
U.S. Appl. No. 17/848,074, filed Jun. 23, 2022 Non-Final Office Action dated Aug. 15, 2024.
U.S. Appl. No. 18/536,087, filed Dec. 11, 2023 Notice of Allowance dated Aug. 29, 2024.
PCT/US2022/011980 filed Jan. 11, 2022 International Search Report and Written Opinion dated Apr. 13, 2022.
PCT/US2022/013007 filed Jan. 19, 2022 International Search Report and Written Opinion dated Apr. 22, 2022.
PCTUS2022011971 filed Jan. 11, 2022 International Search Report and Written Opinion dated Apr. 21, 2022.
U.S. Appl. No. 17/589,849, filed Jan. 31, 2022 Final Office Action dated Jun. 27, 2023.
U.S. Appl. No. 17/589,849, filed Jan. 31, 2022 Non-Final Office Action dated Apr. 12, 2023.
U.S. Appl. No. 17/589,849, filed Jan. 31, 2022 Notice of Allowance dated Aug. 23, 2023.
All in 1: Injection Tracker, posted date unavailable [online], [retrieved Apr. 10, 2025]. Retrieved from internet, https://apps.apple.com/us/app/all-in-1-injection-tracker/id1667540577. (Year: 2025).
Creating an accessible, usable and compelling Injection Site Tracking feature that can used by all our users, posted date May 2020 [u online], [retrieved Apr. 10, 2025]. Retrieved from internet, https://www.bradstricker.com/case-studies/injection-site-tracking. (Year: 2020).
Injection Tracker App, posted date unavailable [online], [retrieved Apr. 10, 2025]. Retrieved from internet, https://www.vladcristei.com/project_page_it. (Year: 2025).
U.S. Appl. No. 17/583,090, filed Jan. 24, 2022 Final Office Action dated Jul. 1, 2025.
U.S. Appl. No. 17/678,965, filed Feb. 23, 2022 Notice of Allowance dated Jun. 3, 2025.
U.S. Appl. No. 17/686,301, filed Mar. 3, 2022 Non-Final Office Action dated May 14, 2025.
U.S. Appl. No. 17/689,791, filed Mar. 8, 2022 Final Office Action dated May 21, 2025.
U.S. Appl. No. 17/690,908, filed Mar. 9, 2022 Final Office Action dated Jun. 24, 2025.
U.S. Appl. No. 17/694,416, filed Mar. 14, 2022 Final Office Action dated Jun. 20, 2025.
U.S. Appl. No. 17/700,216, filed Mar. 21, 2022 Final Office Action dated Jun. 23, 2025.
U.S. Appl. No. 17/709,019, filed Mar. 30, 2022 Final Office Action dated Jun. 15, 2025.
U.S. Appl. No. 17/723,210, filed Apr. 18, 2022 Final Office Action dated May 21, 2025.
U.S. Appl. No. 17/849,419, filed Jun. 24, 2022 Non-Final Office Action dated Jun. 13, 2025.
U.S. Appl. No. 17/857,997, filed Jul. 5, 2022 Non-Final Office Action dated Apr. 28, 2025.
U.S. Appl. No. 17/881,270, filed Aug. 4, 2022 Non-Final Office Action dated Apr. 28, 2025.
U.S. Appl. No. 18/085,566, filed Dec. 20, 2022 Restriction Requirement dated May 16, 2025.
U.S. Appl. No. 29/939,277, filed Apr. 25, 2024 Non-Final Office Action dated May 13, 2025.
Wound care app can help determine appropriate wounddressings, posted date Apr. 24, 2013 [online], [retrieved Apr. 10, 2025]. Retrieved from internet, https://www.imedicalapps.com/2013/04/wound-care-app-dressings/. (Year: 2013).
PCT/US2022/031428 filed May 27, 2022 International Search Report and Written Opinion dated Jan. 30, 2023.
U.S. Appl. No. 17/547,128, filed Dec. 9, 2021 Non-Final Office Action dated Feb. 10, 2025.
U.S. Appl. No. 17/552,309, filed Dec. 15, 2021 Non-Final Office Action dated Mar. 14, 2025.
U.S. Appl. No. 17/552,309, filed Dec. 15, 2021 Restriction Requirement dated Dec. 12, 2024.
U.S. Appl. No. 17/583,090, filed Jan. 24, 2022 Non-Final Office Action dated Feb. 13, 2025.
U.S. Appl. No. 17/584,101, filed Jan. 25, 2022 Non-Final Office Action dated Feb. 5, 2025.
U.S. Appl. No. 17/584,101, filed Jan. 25, 2022 Restriction Requirement dated Nov. 5, 2024.
U.S. Appl. No. 17/678,965, filed Feb. 23, 2022 Non-Final Office Action dated Feb. 12, 2025.
U.S. Appl. No. 17/686,301, filed Mar. 3, 2022 Advisory Action dated Apr. 4, 2025.
U.S. Appl. No. 17/686,301, filed Mar. 3, 2022 Final Office Action dated Jan. 29, 2025.
U.S. Appl. No. 17/689,791, filed Mar. 8, 2022 Non-Final Office Action dated Dec. 30, 2024.
U.S. Appl. No. 17/690,908, filed Mar. 9, 2022 Non-Final Office Action dated Dec. 18, 2024.
U.S. Appl. No. 17/691,990, filed Mar. 10, 2022 Non-Final Office Action dated Dec. 17, 2024.
U.S. Appl. No. 17/694,416, filed Mar. 14, 2022 Non-Final Office Action dated Jan. 22, 2025.
U.S. Appl. No. 17/694,416, filed Mar. 14, 2022 Restriction Requirement dated Nov. 8, 2024.
U.S. Appl. No. 17/700,216, filed Mar. 21, 2022 Non-Final Office Action dated Feb. 5, 2025.
U.S. Appl. No. 17/709,019, filed Mar. 30, 2022 Non-Final Office Action dated Dec. 31, 2024.
U.S. Appl. No. 17/723,210, filed Apr. 18, 2022 Non-Final Office Action dated Dec. 20, 2024.
U.S. Appl. No. 17/848,074, filed Jun. 23, 2022 Notice of Allowance dated Nov. 26, 2024.
U.S. Appl. No. 17/849,419, filed Jun. 24, 2022 Final Office Action dated Feb. 14, 2025.
U.S. Appl. No. 17/849,419, filed Jun. 24, 2022 Non-Final Office Action dated Nov. 8, 2024.
U.S. Appl. No. 17/857,997, filed Jul. 5, 2022 Restriction Requirement dated Feb. 12, 2025.
U.S. Appl. No. 17/859,995, filed Jul. 7, 2022 Non-Final Office Action dated Mar. 11, 2025.
U.S. Appl. No. 17/881,270, filed Aug. 4, 2022 Restriction Requirement dated Feb. 11, 2025.
PCT/US2021/065144 filed Dec. 23, 2021 International Search Report dated Oct. 4, 2022.
PCT/US2022/026999 filed Apr. 29, 2022 International Search Report and Written Opinion dated Oct. 24, 2022.
U.S. Appl. No. 17/848,074, filed Jun. 23, 2022 Advisory Action dated Jul. 9, 2024.
U.S. Appl. No. 17/848,074, filed Jun. 23, 2022 Final Office Action dated Apr. 26, 2024.
U.S. Appl. No. 17/848,074, filed Jun. 23, 2022 Non-Final Office Action dated Nov. 30, 2023.
U.S. Appl. No. 18/536,087, filed Dec. 11, 2023 Non-Final Office Action dated Jun. 28, 2024.

(56) References Cited

OTHER PUBLICATIONS

PCT/US2016/015688 filed Jan. 29, 2016 International Search Report and Written Opinion dated Apr. 1, 2016.
PCT/US2022/013672 filed Jan. 25, 2022, International Search Report and Written Opinion dated Jul. 15, 2022.
PCT/US2022/014147 filed Jan. 27, 2022 International Search Report and Written Opinion dated Jul. 18, 2022.
Lustig et al. "Solute Diffusion in Swollen Membranes. IX. Scaling Laws for Solute Diffusion in Gels", Journal of Applied Polymer Science, vol. 36, pp. 735-747 (Year: 1988).
U.S. Appl. No. 17/547,128, filed Dec. 9, 2021 Advisory Action dated Nov. 19, 2025.
U.S. Appl. No. 17/547,128, filed Dec. 9, 2021 Final Office Action dated Aug. 27, 2025.
U.S. Appl. No. 17/547,128, filed Dec. 9, 2021 Non-Final Office Action dated Dec. 29, 2025.
U.S. Appl. No. 17/552,309, filed Dec. 15, 2021 Advisory Action dated Oct. 2, 2025.
U.S. Appl. No. 17/552,309, filed Dec. 15, 2021 Final Office Action dated Jul. 30, 2025.
U.S. Appl. No. 17/552,309, filed Dec. 15, 2021 Non-Final Office Action dated Nov. 5, 2025.
U.S. Appl. No. 17/583,090, filed Jan. 24, 2022 Notice of Allowance dated Sep. 30, 2025.
U.S. Appl. No. 17/584,101, filed Jan. 25, 2022 Final Office Action dated Oct. 23, 2025.
U.S. Appl. No. 17/686,301, filed Mar. 3, 2022 Advisory Action dated Jan. 14, 2026.
U.S. Appl. No. 17/686,301, filed Mar. 3, 2022 Final Office Action dated Oct. 28, 2025.
U.S. Appl. No. 17/689,791, filed Mar. 8, 2022 Advisory Action dated Jul. 24, 2025.
U.S. Appl. No. 17/689,791, filed Mar. 8, 2022 Non-Final Office Action dated Nov. 5, 2025.
U.S. Appl. No. 17/690,908, filed Mar. 9, 2022 Advisory Action dated Sep. 3, 2025.
U.S. Appl. No. 17/690,908, filed Mar. 9, 2022 Non-Final Office Action dated Oct. 2, 2025.
U.S. Appl. No. 17/691,990, filed Mar. 10, 2022 Advisory Action dated Jul. 24, 2025.
U.S. Appl. No. 17/691,990, filed Mar. 10, 2022 Non-Final Office Action dated Aug. 28, 2025.
U.S. Appl. No. 17/694,416, filed Mar. 14, 2022 Advisory Action dated Aug. 20, 2025.
U.S. Appl. No. 17/694,416, filed Mar. 14, 2022 Non-Final Office Action dated Oct. 1, 2025.
U.S. Appl. No. 17/697,879, filed Mar. 17, 2022 Non-Final Office Action dated Sep. 30, 2025.
U.S. Appl. No. 17/700,216, filed Mar. 21, 2022 Advisory Action dated Oct. 9, 2025.
U.S. Appl. No. 17/700,216, filed Mar. 21, 2022 Non-Final Office Action dated Dec. 3, 2025.
U.S. Appl. No. 17/709,019, filed Mar. 30, 2022 Advisory Action dated Jul. 24, 2025.
U.S. Appl. No. 17/709,019, filed Mar. 30, 2022 Non-Final Office Action dated Nov. 19, 2025.
U.S. Appl. No. 17/723,210, filed Apr. 18, 2022 Advisory Action dated Jul. 31, 2025.
U.S. Appl. No. 17/723,210, filed Apr. 18, 2022 Non-Final Office Action dated Dec. 29, 2025.
U.S. Appl. No. 17/848,039, filed Jun. 23, 2021 Non-Final Office Action dated Jul. 29, 2025.
U.S. Appl. No. 17/848,039, filed Jun. 23, 2022 Final Office Action dated Dec. 29, 2025.
U.S. Appl. No. 17/849,419, filed Jun. 24, 2022 Notice of Allowance dated Jan. 29, 2026.
U.S. Appl. No. 17/857,997, filed Jul. 5, 2022 Final Office Action dated Oct. 27, 2025.
U.S. Appl. No. 17/859,995, filed Jul. 7, 2022 Advisory Action dated Oct. 28, 2025.
U.S. Appl. No. 17/859,995, filed Jul. 7, 2022 Final Office Action dated Aug. 22, 2025.
U.S. Appl. No. 17/859,995, filed Jul. 7, 2022 Non-Final Office Action dated Dec. 23, 2025.
U.S. Appl. No. 17/881,270, filed Aug. 4, 2022 Advisory Action dated Jan. 14, 2026.
U.S. Appl. No. 17/881,270, filed Aug. 4, 2022 Final Office Action dated Oct. 27, 2025.
U.S. Appl. No. 18/085,566, filed Dec. 20, 2022 Non-Final Office Action dated Oct. 1, 2025.
U.S. Appl. No. 18/272,026, filed Jul. 12, 2023 Non-Final Office Action dated Jul. 31, 2025.
U.S. Appl. No. 18/272,332, filed Jul. 13, 2023 Restriction Requirement dated Jan. 21, 2026.
U.S. Appl. No. 18/273,163, filed Jul. 19, 2023 Restriction Requirement dated Nov. 6, 2025.
U.S. Appl. No. 18/274,156, filed Jul. 25, 2023 Non-Final Office Action dated Oct. 1, 2025.
U.S. Appl. No. 18/274,436, filed Jul. 26, 2023 Non-Final Office Action dated Oct. 1, 2025.
U.S. Appl. No. 18/289,341, filed Nov. 2, 2023 Restriction Requirement dated Nov. 6, 2025.
U.S. Appl. No. 19/068,969, filed Mar. 3, 2025 Non-Final Office Action dated Dec. 29, 2025.
U.S. Appl. No. 29/939,277, filed Apr. 25, 2024 Restriction Requirement dated Oct. 2, 2025.
U.S. Appl. No. 17/547,128, filed Dec. 9, 2021 Final Office Action dated Apr. 6, 2026.
U.S. Appl. No. 17/686,301, filed Mar. 3, 2022 Non-Final Office Action dated Apr. 3, 2026.
U.S. Appl. No. 17/691,990, filed Mar. 10, 2022 Final Office Action dated Mar. 9, 2026.
U.S. Appl. No. 17/694,416, filed Mar. 14, 2022 Final Office Action dated Apr. 9, 2026.
U.S. Appl. No. 17/697,879, filed Mar. 17, 2022 Non-Final Office Action dated Mar. 26, 2026.
U.S. Appl. No. 17/848,039, filed Jun. 23, 2022 Notice of Allowance dated Apr. 13, 2026.
U.S. Appl. No. 18/085,566, filed Dec. 20, 2022 Final Office Action dated Mar. 9, 2026.
U.S. Appl. No. 18/272,026, filed Jul. 12, 2023 Final Office Action dated Dec. 31, 2025.
U.S. Appl. No. 18/272,026, filed Jul. 12, 2023 Notice of Allowance dated Mar. 27, 2026.
U.S. Appl. No. 18/272,332, filed Jul. 13, 2023 Non-Final Office Action dated Mar. 25, 2026.
U.S. Appl. No. 18/273,163, filed Jul. 19, 2023 Non-Final Office Action dated Feb. 3, 2026.
U.S. Appl. No. 18/274,156, filed Jul. 25, 2023 Final Office Action dated Mar. 25, 2026.
U.S. Appl. No. 18/274,436, filed Jul. 26, 2023 Final Office Action dated Mar. 25, 2026.
U.S. Appl. No. 18/289,341, filed Nov. 2, 2023 Non-Final Office Action dated Feb. 18, 2026.
U.S. Appl. No. 18/715,504, filed May 31, 2024 Non-Final Office Action dated Apr. 9, 2026.
U.S. Appl. No. 18/715,504, filed May 31, 2024 Restriction Requirement dated Feb. 4, 2026.
U.S. Appl. No. 18/832,782, filed Jul. 24, 2024 Non-Final Office Action dated Apr. 20, 2026.
U.S. Appl. No. 29/939,277, filed Apr. 25, 2024 Ex Parte Quayle Action dated Feb. 23, 2026.
Advantage Engineering, "Proper Use of Inhibited Propylene Glycol", Jun. 12, 2001, http://www.ttequip.com/knowledgelibrary/Proper%20Use%20Of%20Inh-ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g-us.edu/hbase/tables.thron.html Jul. 31, 2010.
Murray, R. Z., et al. "Development and use of biomaterials as wound healing therapies" Burns & Trauma (2019) 7:2 https://doi.org/10.1186/s41038-018-0139-7 (2019).

(56) References Cited

OTHER PUBLICATIONS

PCT/US2015/045548 filed Aug. 17, 2015 International Search Report and Written Opinion dated Nov. 24, 2015.
Sevgi, M., et al. "Topical Antimicrobials for Bum Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021.
U.S. Appl. No. 17/552,309 filed Dec. 15, 2021 Final Office Action dated Apr. 22, 2026.
U.S. Appl. No. 17/584,101 filed Jan. 25, 2022 Non-Final Office Action dated May 14, 2026.
U.S. Appl. No. 17/689,791 filed Mar. 8, 2022 Final Office Action dated Apr. 22, 2026.
U.S. Appl. No. 17/690,908 filed Mar. 9, 2022 Final Office Action dated May 12, 2026.
U.S. Appl. No. 17/691,990 filed Mar. 10, 2022 Advisory Action dated May 27, 2026.
U.S. Appl. No. 17/709,019 filed Mar. 30, 2022 Final Office Action dated Apr. 22, 2026.
U.S. Appl. No. 17/723,210 filed Apr. 18, 2022 Final Office Action dated May 5, 2026.
U.S. Appl. No. 17/859,995 filed Jul. 7, 2022 Final Office Action dated Apr. 28, 202.
U.S. Appl. No. 18/085,566 filed Dec. 20, 2022 Advisory Action dated May 14, 2026.
U.S. Appl. No. 18/274,156 filed Jul. 25, 2023 Notice of Allowance dated Jun. 9, 2026.
U.S. Appl. No. 18/274,436 filed Jul. 26, 2023 Notice of Allowance dated Jun. 10, 2026.
U.S. Appl. No. 18/837,098 filed Aug. 8, 2024 Non-Final Office Action dated Apr. 22, 2026.
U.S. Appl. No. 19/068,969 filed Mar. 3, 2025 Non-Final Office Action dated Apr. 28, 2026.
U.S. Appl. No. 29/939,277 filed Apr. 25, 2024 Notice of Allowance dated Jun. 10, 2026.

* cited by examiner

THERMAL PAD WITH ENHANCED HEAT TRANSFER CHARACTERISTICS

PRIORITY

This application claims the benefit of priority to U.S. Provisional Application No. 63/213,099, filed Jun. 21, 2021, which is incorporated by reference in its entirety into this application.

BACKGROUND

The effect of temperature on the human body has been well documented and the use of targeted temperature management (TTM) systems for selectively cooling and/or heating bodily tissue is known. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Targeted temperature management can be viewed in two different aspects. The first aspect of temperature management includes treating abnormal body temperatures, i.e., cooling the body under conditions of hyperthermia or warming the body under conditions of hypothermia. The second aspect of thermoregulation is an evolving treatment that employs techniques that physically control a patient's temperature to provide a physiological benefit, such as cooling a stroke patient to gain some degree of neuroprotection. By way of example, TTM systems may be utilized in early stroke therapy to reduce neurological damage incurred by stroke and head trauma patients. Additional applications include selective patient heating/cooling during surgical procedures such as cardiopulmonary bypass operations.

TTM systems circulate a fluid (e.g., water) through one or more thermal contact pads coupled to a patient to affect thermal energy exchange with the patient. The total rate of thermal energy exchange is directly is related to the pad to patient contact area and the specific rate of energy exchange across the contact area. The specific rate of energy exchange is defined by the temperature difference between the body temperature and the water temperature and the efficiency of the thermal connection between the water and the patient.

Increasing the total rate of thermal energy exchange can shorten the time required adjust the patient's body temperature. While the total rate of thermal energy exchange may be increased by increasing the temperature difference, extreme temperature differences produce other negative effects. Extreme temperature differences require additional power to heat or cool the water. Extreme temperature differences can also result in patient discomfort due to hot and cold spots across the contact pad. As such, increasing total thermal exchange while minimizing the temperature difference may be generally more preferred.

As patient sizes and shapes vary, it may be difficult to optimize the pad to patient contact area limiting total energy exchange. A pad's internal water flow characteristics may also limit total energy exchange via limited convective heat transfer. Thermal pad materials may also limit conductive heat transfer. Disclosed herein are embodiments of devices and methods for the improvement of total thermal energy exchange rate during a TTM procedure without increasing the temperature difference between the water and the patient.

SUMMARY OF THE INVENTION

Briefly summarized, disclosed herein is a medical pad for exchanging thermal energy between a targeted temperature management (TTM) fluid and a patient. The pad includes a fluid channel extending between a fluid inlet and a fluid outlet, and a bottom channel wall that is disposed between the fluid and the patient during use of the pad. The wall is formed of a material having a thermal conductivity, and the wall includes elements embedded within the wall. The elements are formed of a material having a greater thermal conductivity than the wall material so that a composite thermal conductivity of the wall is greater than the thermal conductivity of the wall material alone. The thermal energy exchange between the fluid and the patient is defined in accordance with the composite thermal conductivity. The elements may include one or more of particles, nanoparticles, composites, fibers, fluid pockets, bars extending across the thickness of the wall, or layers extending along the wall.

The fluid channel may include channel portions disposed laterally adjacent one another which also may be arranged parallel to one another. The channel portions may also be separated by a single dividing wall and in some embodiments, the fluid flow in adjacent channel portions is in opposite directions.

In some embodiments, the channel defines a spiral shape converging radially inward from an inlet positioned at a permitter edge of the pad toward an outlet centrally positioned on the pad. In other embodiments, the channel defines a double spiral shape including a first channel portion converging radially inward from an inlet disposed at a permitter edge of the pad toward a central location of the pad and a second channel portion expanding radially outward from the central location toward an outlet disposed at the permitter edge of the pad. The channel portions are fluid connected together at the central location, and the second channel portion is disposed between adjacent wraps of the first channel portion.

Centrifugal acceleration of the fluid flow within the spiraling channel induces turbulence of the fluid flow within the channel, which in turn defines a first enhancement of a convection coefficient of the fluid with respect to the bottom wall, and the thermal energy exchange between the fluid and the patient is defined in accordance with a convection coefficient including the first enhancement.

In some embodiments, the channel includes at least one pair of channel walls extending along the channel, and the channel walls face each other from opposite sides of the channel. The channel further includes a plurality of wall segments extending across at least a majority of the channel, including a first subset of the wall segments extending away from one channel wall, and a second subset of the wall segments extending away from the other channel wall. Each wall segment of the second subset is disposed between adjacent wall segments of the first subset. Fluid flow between the wall segments induces turbulence of the fluid flow within the channel, which defines a second enhancement of the convection coefficient of the fluid with respect to the bottom wall, and the thermal energy exchange between the fluid and the patient is defined in accordance with the convection coefficient including the second enhancement.

In some embodiments, the channel comprises a plurality of inward protruding ribs disposed along one or more walls of the channel. The ribs are disposed at an angle with respect to the channel to induce a swirling turbulence of the fluid flow along the channel. The swirling turbulence defines a third enhancement of the convection coefficient of the fluid with respect to the bottom wall, and the thermal energy exchange between the fluid and the patient is defined in accordance with the convection coefficient including the third enhancement.

In some embodiments, the pad includes a first pad portion defining a first patient contact area and a separate second pad portion defining a second patient contact area. The second pad portion is directly coupleable with the first pad portion to define a combined patient contact area equaling a sum of the first patient contact area and the second patient contact area.

In other embodiments, a patient contact area of the pad includes a first patient contact area defined by a first pad portion and a second patient area defined by a second pad portion. The second pad portion is separable from the first pad portion to define a reduced patient contact area equaling the first patient contact area.

Also disclosed herein is a method of providing a targeted temperature management (TTM) therapy to a patient. The method includes (i) applying a thermal contact pad to a patient, (ii) altering a patient contact area of the pad to accommodate a size of the patient, and (iii) establishing a flow of TTM fluid through the pad.

The step of altering the patient contact area may include coupling a second thermal contact pad to the thermal contact pad to increase the patient contact area.

The step of altering the patient contact area may also include removing a separable portion of the thermal contact pad from the thermal contact pad to decrease the patient contact area to an area defined by a remaining portion of the thermal contact pad.

The step of establishing a flow of TTM fluid may include directing TTM fluid flow along a spiraling fluid channel to enhance a heat transfer convection coefficient of the thermal pad.

The step of establishing a flow of TTM fluid may also include directing TTM fluid flow along a fluid channel configured to enhance the heat transfer convection coefficient of the thermal pad. The fluid channel comprises at least one pair of channel walls extending along the channel, and the channel walls face each other from opposite sides of the channel. The channel further includes a plurality of wall segments extending across at least a majority of the channel, including a first subset of the wall segments extending away from one of the pair of channel walls and a second subset of the wall segments extending away from the other of the pair of channel walls. Each wall segment of the second subset is disposed between adjacent wall segments of the first subset.

The method may further include exchanging thermal energy with the patient through a bottom wall of the thermal contact pad, where the bottom wall includes embedded elements configured to enhance a thermal conductivity of the bottom wall.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1A:
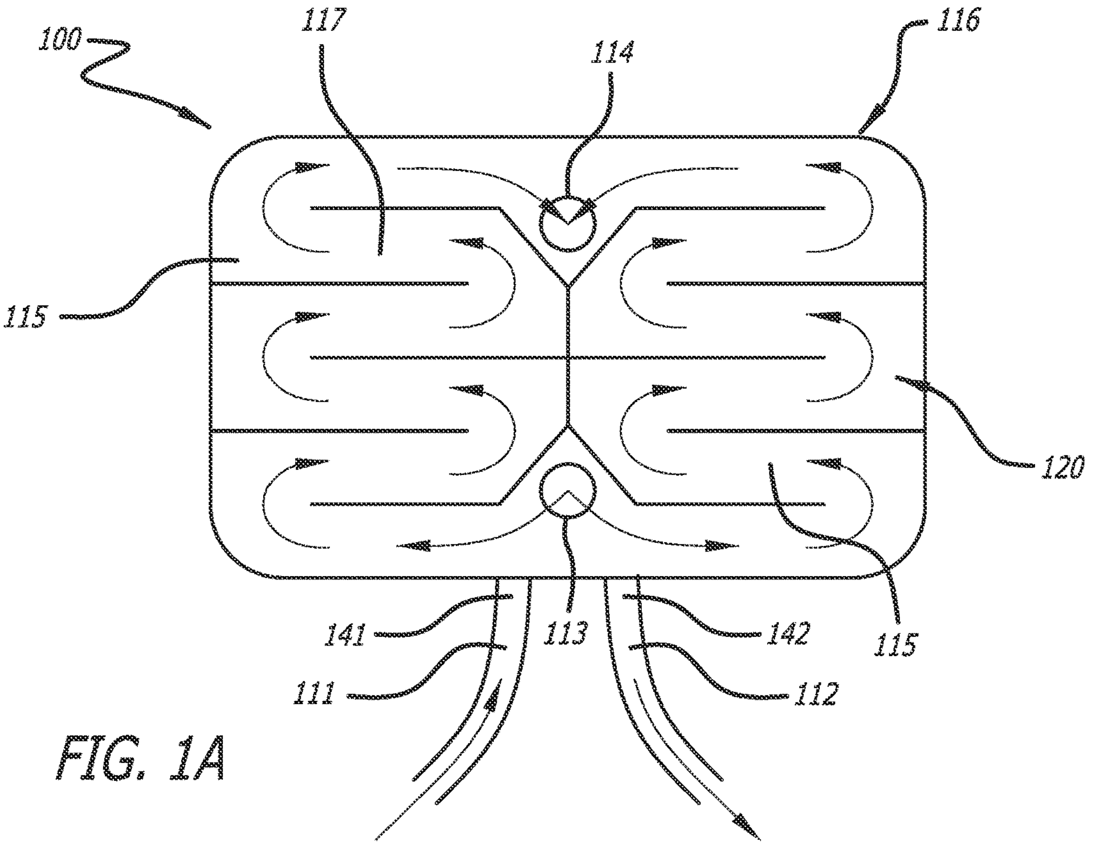
FIG. 1A illustrates a current embodiment of a thermal contact pad for use with a targeted temperature management (TTM) system for cooling or warming a patient, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising." Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled to" refer to any form of interaction between two or more entities, including mechanical, electrical, magnetic, electromagnetic, fluid, signal, communicative (including wireless), and thermal interaction. Two components may be connected or coupled to each other even though they are not in direct contact with each other. For example, two components may be coupled to each other through an intermediate component.

Unless defined otherwise, all technical and scientific terms used herein have the same meaning as commonly understood by those of ordinary skill in the art.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

FIG. 1A illustrates a bottom view of a current embodiment of a thermal contact pad 100 for use in performing a targeted temperature management (TTM) treatment on a patient. The pad 100 is configured for affecting thermal energy transfer between a liquid 120 (typically water) and the patient (not shown). The pad 100 receives the water 120 from a TTM system (not shown) via a fluid delivery conduit 111 and returns the water 120 to the TTM system via a fluid return conduit 112. The water 120 enters the pad 100 through an entry port 113 and exits the pad 100 through an exit port 114. Between the entry port 113 and the exit port 114, the water flows through a pair of channels 115. The channels 115 are sized and arranged to extend across (i.e., cover) an entire contact area 116 of the pad 100. The channels 115 are arranged in a serpentine fashion so that the fluid flow in adjacent channels is in opposite directions.

The water 120 enters the pad 100 at an inlet temperature 141 and exits the pad 100 at an outlet temperature 142. In use, the temperature of the water gradually transitions from the inlet temperature 141 to the outlet temperature 142. In some treatment scenarios, the TTM treatment parameters are defined to increase a body temperature. In such instances, the inlet temperature 141 is greater than the body temperature and the gradually cools down along the channel 115 to the outlet temperature 142. In other scenarios, the TTM treatment parameters are defined to decrease a body temperature. In these instances, the inlet temperature 141 is less than the body temperature and the gradually warms up to the outlet temperature 142.

In use, the pad 100 is applied to the patient so that the bottom surface 117 is in direct contact with the skin of the patient. The inlet water temperature 141 is defined in accordance with the desired treatment and water flow is initiated. In some instances, a core temperature of the patient is monitored to assess the progress of the treatment.

Figure 1B:
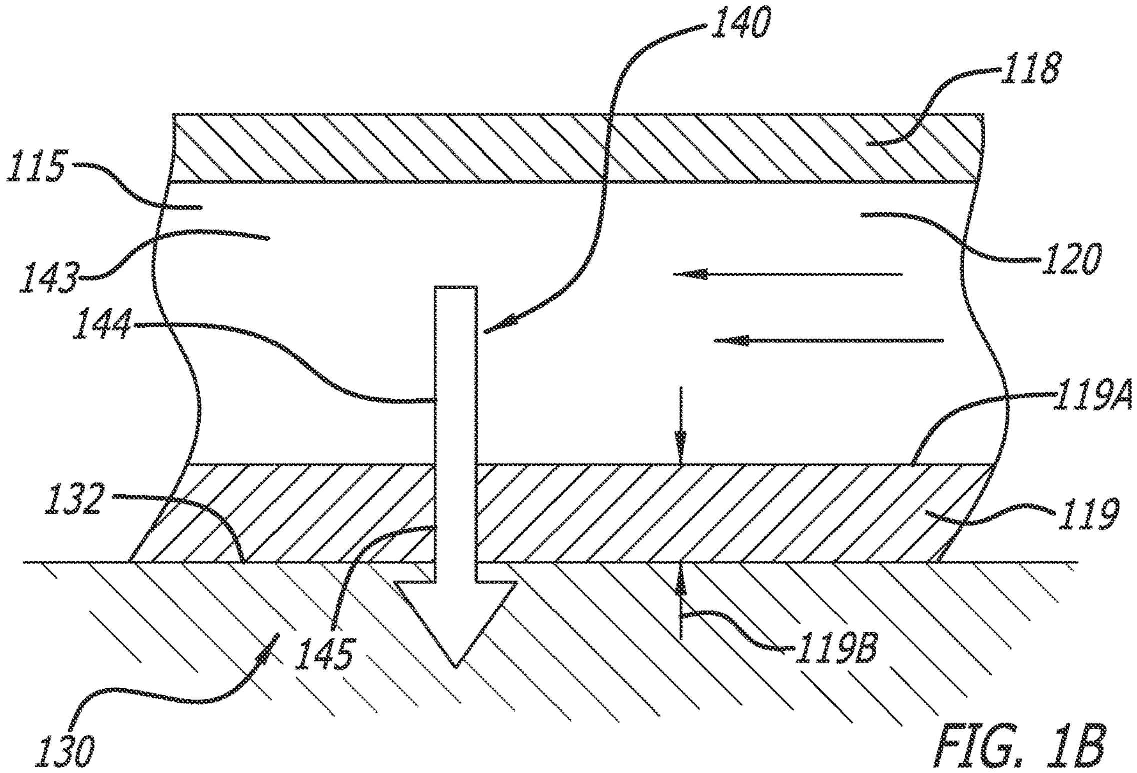
FIG. 1B illustrates a thermal energy transfer model between a TTM fluid and a patient, in accordance with some embodiments.

FIG. 1B is an illustration of a heat transfer model of the pad of FIG. 1A. FIG. 1B illustrates an exemplary cross-sectional view of a channel 115 of the pad 100 in contact with a skin surface 132 of the patient 130. The pad 100 includes the channel 115 sandwiched between a top wall 118 and a bottom wall 119. Water 120 flows through the channel 115 at an average temperature 143. In the illustrated model, heat transfer 140 (i.e., thermal energy transfer) is directed from the water 120 to the patient 130. In an alternative model, the heat transfer 140 may be directed from the patient 130 to the water 120. In either model, the mathematical model described below applies equally.

The heat transfer 140 initially occurs from the water 120 to the inside wall surface 119A of the bottom wall 119 by way of convection 144 as described below. The heat transfer 140 then passes across a thickness 119C of the wall 119 from the surface inside 119A to the skin surface 132 by way of conduction as also described below.

The heat transfer 140 by way of convection 144 from the water 120 to the surface 119A may be estimated by the convection equation 1 below.

$$Q_{cv} = hA(T_l - T_w) \quad \text{Equation 1}$$

$Q_{cv}$ is the convective heat transfer in Watts (W).

t is the pad-wall thickness in meters (m).

A is the pad area in square meters ($m^2$)

$T_l$ is the average temperature of the liquid in degrees Celsius (° C.)

$T_w$ is the temperature of the inside surface of the pad wall in ° C.

h is the convection coefficient of the liquid in Watts/$m^{2}$° C.

The heat transfer 140 by way of conduction 145 from the surface 119A to the skin surface 132 may be estimated by the conduction equation below.

$$Q_{cd} = \frac{k}{t}A(T_w - T_s) \quad \text{Equation 2}$$

$Q_{cd}$ is the conductive heat transfer in Watts (W).

t is the thickness of pad-wall in meters (m).

A is the area of the pad in square meters ($m^2$)

$T_s$ is the temperature of the skin surface in degrees Celsius (° C.).

$T_w$ is the temperature of the inside surface of the pad wall in ° C.

k is the thermal conductivity of the pad-wall material in W/m ° C.

Combining the convection equation 1 and the conduction equation 2 yields a combined heat transfer equation 3 that may estimate the heat transfer 140 from the pad 100 to the patient 130 in accordance with the model shown and described above.

$$Q_c = A\frac{kh}{k+th}(T_l - T_s) \quad \text{Equation 3}$$

Qc is the combined heat transfer in Watts (W).

t is the thickness of the pad wall in meters (m).

A is the pad area in square meters ($m^2$)

$T_l$ is the average temperature of the liquid in degrees Celsius (° C.)

$T_s$ is the temperature of the skin surface in ° C.

k is the thermal conductivity of the pad-wall material in W/m ° C.

h is the convection coefficient of the liquid in Watts/$m^{2\circ}$ C.

Per the equation 3 above, the combined heat transfer 140 may be increased by increasing or decreasing one more input variables of the equation 3. For example, the heat transfer 140 may be enhanced by increasing the area of the pad 116. The heat transfer 140 may also be enhanced by increasing the thermal conductivity "k" of the pad-wall material and/or increasing the convection coefficient "h.". Shown and described below are thermal pads having enhanced heat transfer features and properties in accordance with equation 3.

Figure 2A:
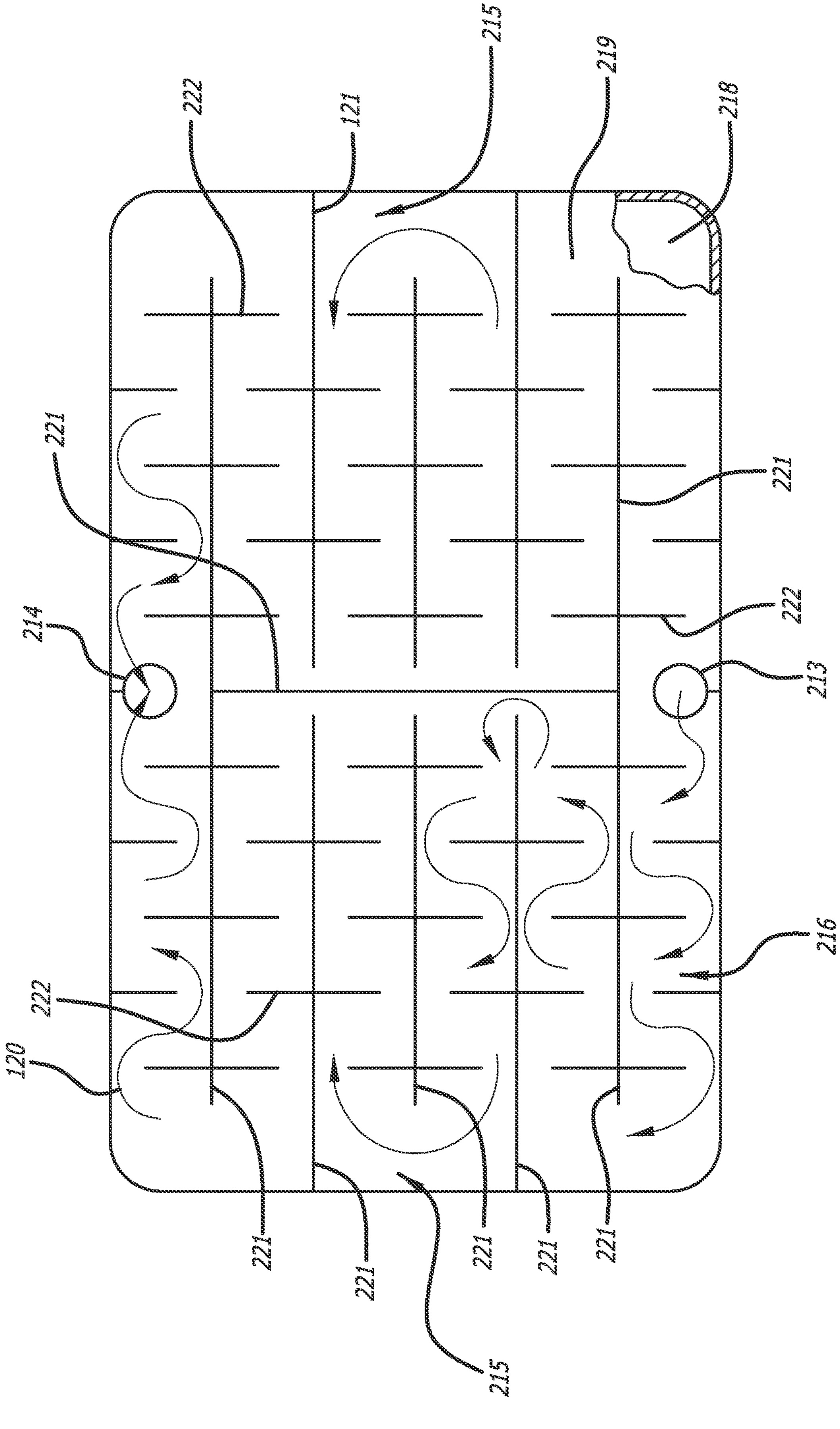
FIG. 2A illustrates a first embodiment of an improved thermal contact pad, in accordance with some embodiments.

FIG. 2A is a bottom view illustration of an improved thermal contact pad 200. The pad 200 includes one or more main flow channels 215 similar to the channels 115 of FIG. 1A. The main channels 215 extend across the pad 200 to cover the entire area 216 of the pad 200. The main channels 215 as are formed by dividing walls 221 that extend between the top wall 218 and a bottom wall 219 of the pad 200. Flow enters the main channels 215 via the entry port 213 and exits via the exit port 214.

The pad 200 further includes protruding wall sections 222 that extend partially across the main channel 215. In some embodiments, the protruding wall sections 222 extend across at least a majority of the main channel 215. Adjacent wall sections 222 extend away from opposite sides of the main channel 215 defining sub-channels 216 arranged in a serpentine fashion along main channel 215. In the illustrated embodiment, the wall sections 222 protrude away from opposite dividing walls 221. In other embodiments, the wall sections 222 may protrude away from the top wall 218 and the bottom wall 219. In still other embodiments, a subset of wall sections 222 may protrude away from the top wall 218 and the bottom wall 219, and another subset of wall sections 222 may protrude away from dividing walls 221.

As may be appreciated by one of ordinary skill, the convection coefficient "h" of equations 1 and 3 above is positively affected by turbulence of the fluid flow along a channel 215. The sub-channels 116 enhance turbulence as the water 120 flows along the main channels 215. The turbulence enhances the convection coefficient "h" causing enhanced heat transfer 140 from the water 120 to the patient 130 as discussed above.

Figure 2B:
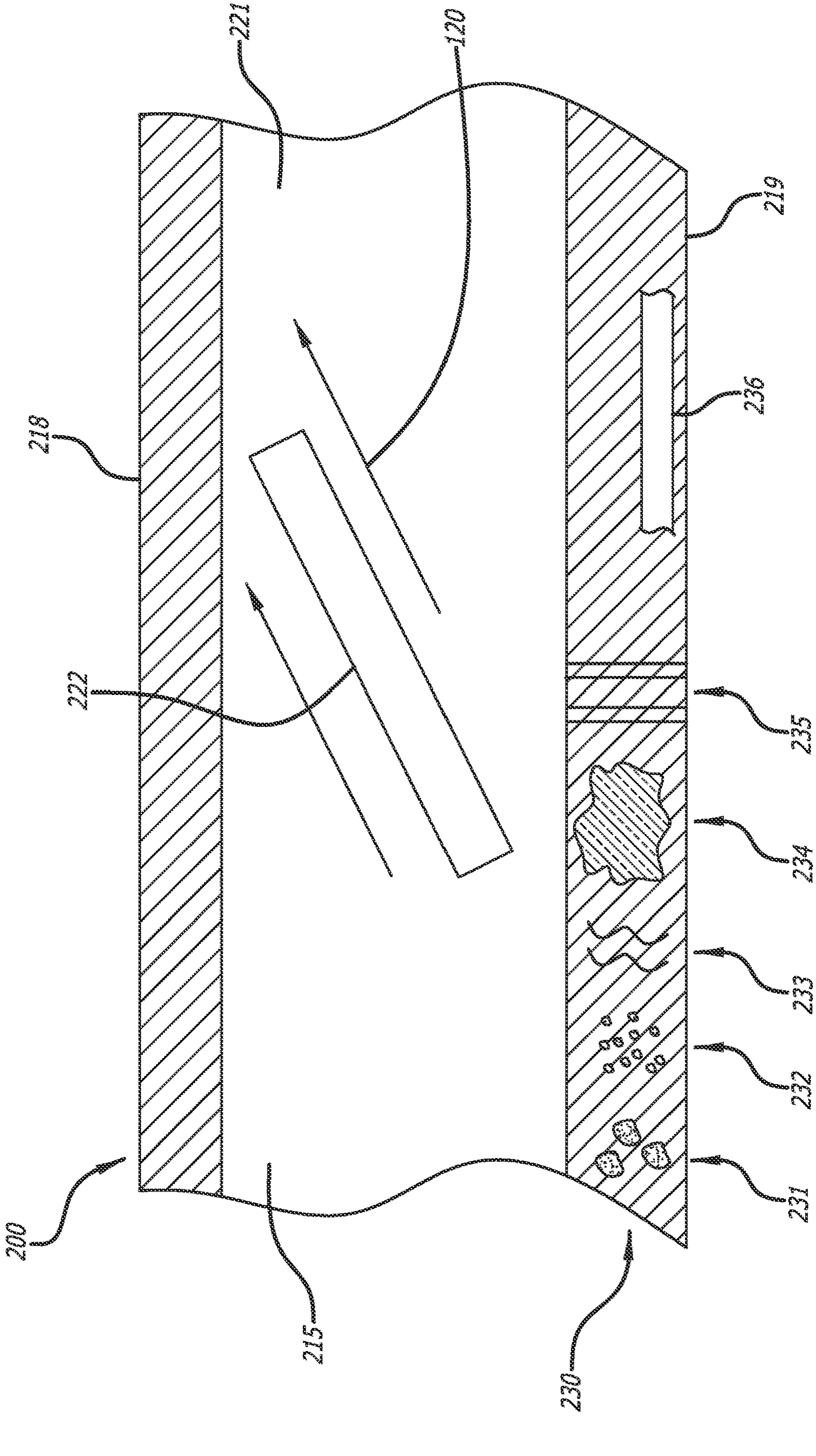
FIG. 2B is a detailed illustration of a portion of the thermal contact pad of FIG. 2A, showing optional components for increasing thermal energy transfer between the TTM fluid and the patient, in accordance with some embodiments.

FIG. 2B is a detailed cross-sectional view of a portion of a channel 215 of the pad 200. The bottom wall 219 may include components or features to enhance the conductive heat transfer 145 (FIG. 1B) through the bottom wall 219. In some embodiments, material of the bottom wall 219 may comprise a material formulation specifically configured for enhanced thermal conductivity. In some embodiments, the material of the bottom wall 219 may comprise a thermal conductivity ("k" in equations 2 and 3) exceeding about 1 W/m° C., 5 W/m° C., 10 W/m° C., 20 W/m° C., or more. In some embodiment, the bottom wall 219 may be formed of a composite material including 2 or more raw materials combined together in a homogenesis or heterogeneous fashion.

In some embodiments, the bottom wall 219 may include conductivity-enhancing components 230 in combination with the material to increase the effective thermal conductivity of the bottom wall 219. The components 230 may be embedded or partially embedded within the wall 219. Exemplary components 230 may include particles 231 of a material having a relatively high thermal conductivity "k" such as aluminum, copper, and the like. The particles 231 may include nano-particles 232. Exemplary components 230 may also include fibers 233 including wires formed of a high-conductive material. Exemplary components 230 may include pockets of a high-conductive liquid substance 234. Exemplary components 230 may include bars of high-conductive material extending through the wall 219. Exemplary components 230 may include one or more layers 236 high-conductive material extending along the wall 219. In some embodiments, the components 230 may include a combination of 2 or more of the exemplary components 231-236.

In some embodiments, the pad 200 may include additional convection enhancing features along the channels 215. For example, additional features may include ribs 223 disposed along the inside surface of the channel 215 and protrude away from the inside surface. The ribs 223 may be disposed on the dividing wall 221, the bottom wall 219, or the top wall 218. The ribs 223 may oriented at an angle with respect to the flow direction of the water 120 (e.g., in a helical fashion) along the channel 215 so as to induce a swirling turbulence of the water 120 along the channel 215. The rotation of the water 120 may enhances the convection coefficient "h." The additional features may also include troughs, bumps, depressions, or a rough surface.

Figure 3:
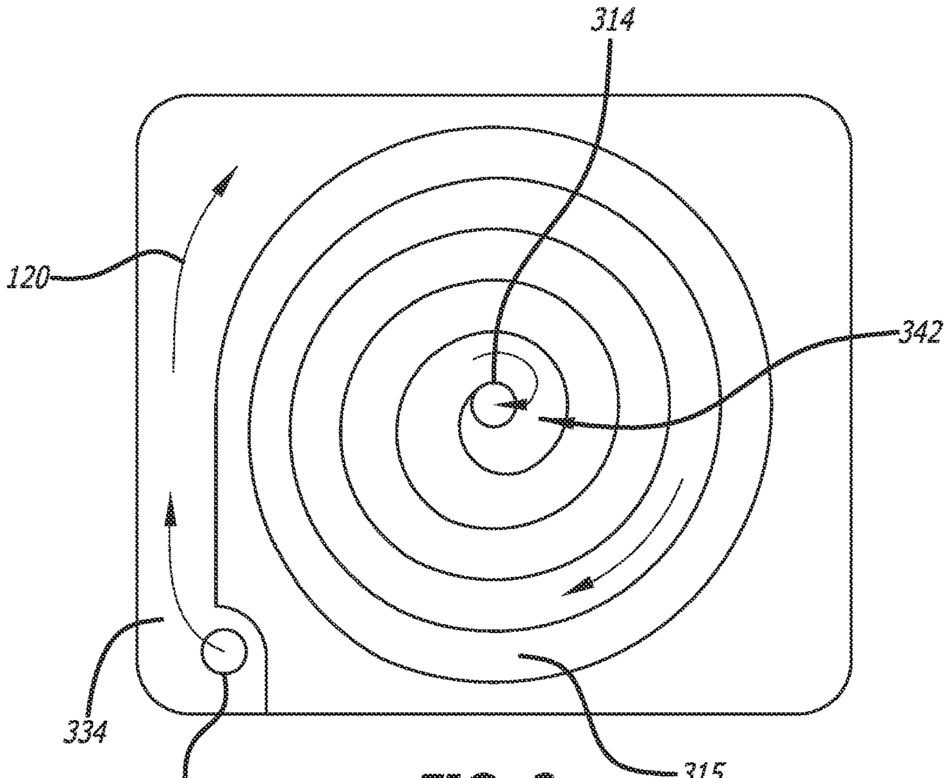
FIG. 3 illustrates a second embodiment of a thermal contact pad having a spiraling fluid channel, in accordance with some embodiments.

FIG. 3 illustrates a second embodiment of a pad 300 defining a spiraling main channel 315. Water 120 enters the channel 315 through the entry port 313 disposed at an edge of the pad 300. The spiraling channel 315 converges radially inward toward the centrally located exit port 314. The spiraling path of the channel 315 generates a centrifugal acceleration of the water 120 as it flows along the channel 316. The centrifugal acceleration causes enhanced turbulence in the water 120 to increase the convection coefficient thereby enhancing the heat transfer 140.

The inward convergence of the spiraling channel 315 may provide an additional advantage. As the water 120 enters the entry port 313, the water 120 initially flows along the circumferential edge of the pad 300. As described above, the inlet temperature 341 of the water 120 cools toward the outlet temperature 342. As the heat transfer 140 is proportional to the temperature difference between the water temperature and the skin temperature (i.e., $T_l$ minus $T_s$ as shown in equation 3), a localized heat transfer 140 along the circumference edge may be greater than a localized heat transfer 140 toward the center of the pad 300. A greater localized heat transfer 140 along the circumferential edge may account for a loss of thermal energy radially away from the circumferential edge thereby defining a more uniform heat transfer 140 across the contact area of the pad 300.

A second advantage of the inward convergence is an increased centrifugal acceleration due to the shorter radius of curvature near the center of the pad 300. As the inlet water temperature 341 along the circumferential edge of the pad 300 approaches the cooler exit temperature 342 near the center of the pad 300, the increased centrifugal acceleration may enhance the convection coefficient "h." The enhanced convection coefficient "h" may account for the decrease in the temperature difference (i.e., Ti minus $T_s$ as shown in equation 3) as the inlet temperature 341 approaches the outlet temperature 342.

Figure 4:
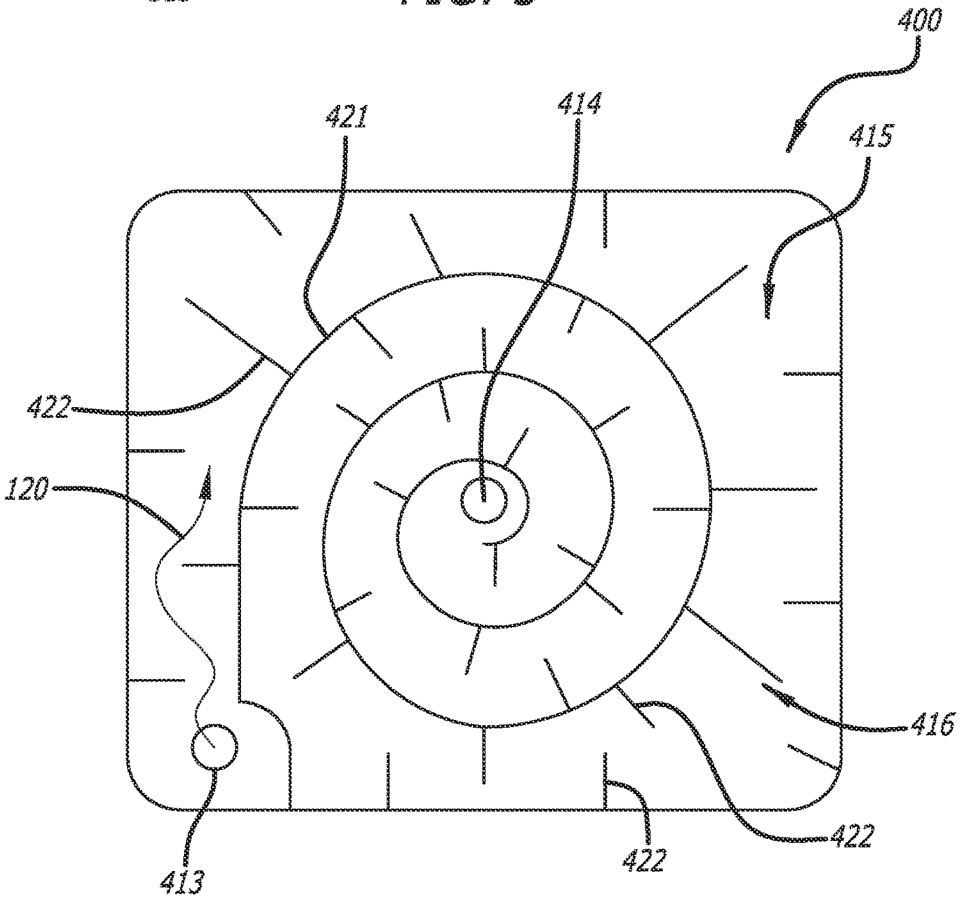
FIG. 4 illustrates a third embodiment of a thermal contact pad having a spiraling fluid channel with increased fluid turbulence, in accordance with some embodiments.

FIG. 4 illustrates a third embodiment of a pad 400 having features similar to the pad 300 of FIG. 3. The pad 400 includes an out-to-in spiraling main channel 415 extending from an entry port 413 positioned at a permitter edge of the pad 400 to the exit port 414 positioned toward the center of the pad 400. As such, the pad 400 may include any or all of the features and functionalities of the pad 300.

The pad 400 includes a dividing wall 421 between adjacent wraps of the main channel 415. The pad 400 further includes protruding wall sections 422 that extend partially across the main channel 415 similar to the protruding wall sections 422 of the pad 200 of FIG. 2A. Adjacent wall sections 422 protrude from opposite sides of the main channel 415 defining sub-channels 416 arranged in a serpentine fashion along main channel 415 to enhance the flow turbulence of the water 120.

Figure 5:
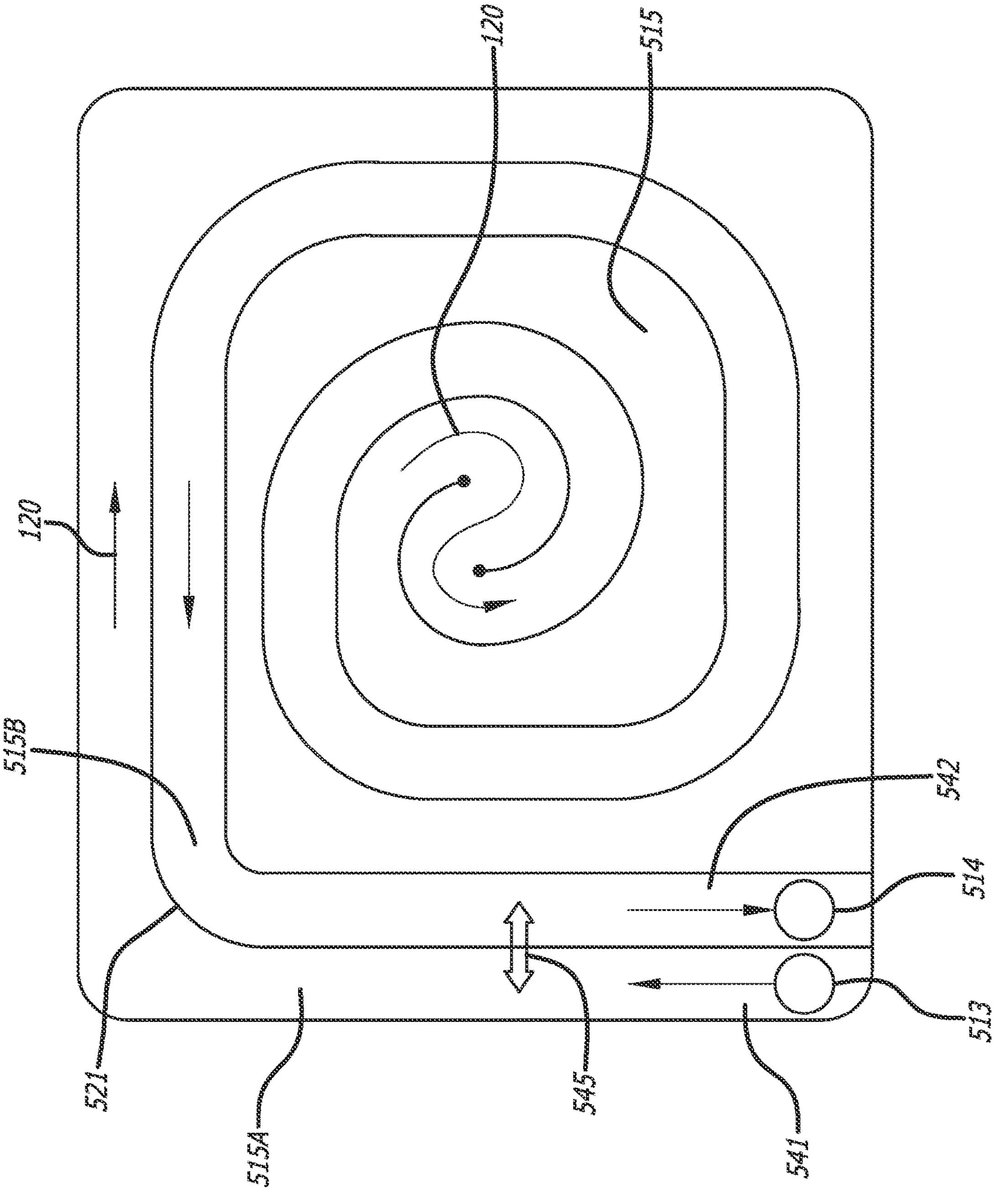
FIG. 5 illustrates a fourth embodiment of a thermal contact pad having a spiraling fluid channel including an inward spiraling first fluid channel portion and an outward spiraling second fluid channel portion, in accordance with some embodiments.

FIG. 5 illustrates a fourth embodiment of a pad 500 the may including features similar to the pads 300 and 400 shown and described above. The pad 500 includes a spiraling main channel 515. A first channel portion 515A begins at the entry port 513 located adjacent the circumferential edge of the pad 500 and converges inward toward the center of the pad 500. A second channel portion 515B begins at the center of the pad 500 and progresses radially outward toward the exit port 514 located adjacent the entry port 513. The first channel portion 515A and the second channel portion 515B are positioned adjacent one another along at least a portion of their respective lengths and in some embodiments, along their entire respective lengths. In the illustrated embodiment, the first channel portion 515A and the second channel portion 515B are separated by a single dividing wall 521. The direction of fluid flow in the second channel portion 515B is opposite to the direction of fluid flow in the first channel portion 515B.

The adjacent positioning of the first channel portion 515A and the second channel portion 515B in combination with the cooling of the water temperature from the inlet temperature 541 to the outlet temperature 542, may facilitate a more consistent heat transfer 140 (FIG. 1B) across the pad 500. For example, the lateral heat transfer 545 between the water 120 in first channel portion 515A and the water 120 in second channel portion 515B, may cause a more uniform temperature of the water along the complete channel 515 thereby defining a more consistent temperature difference (i.e., $T_l$ minus $T_s$ as shown in equation 3).

Figure 6A:
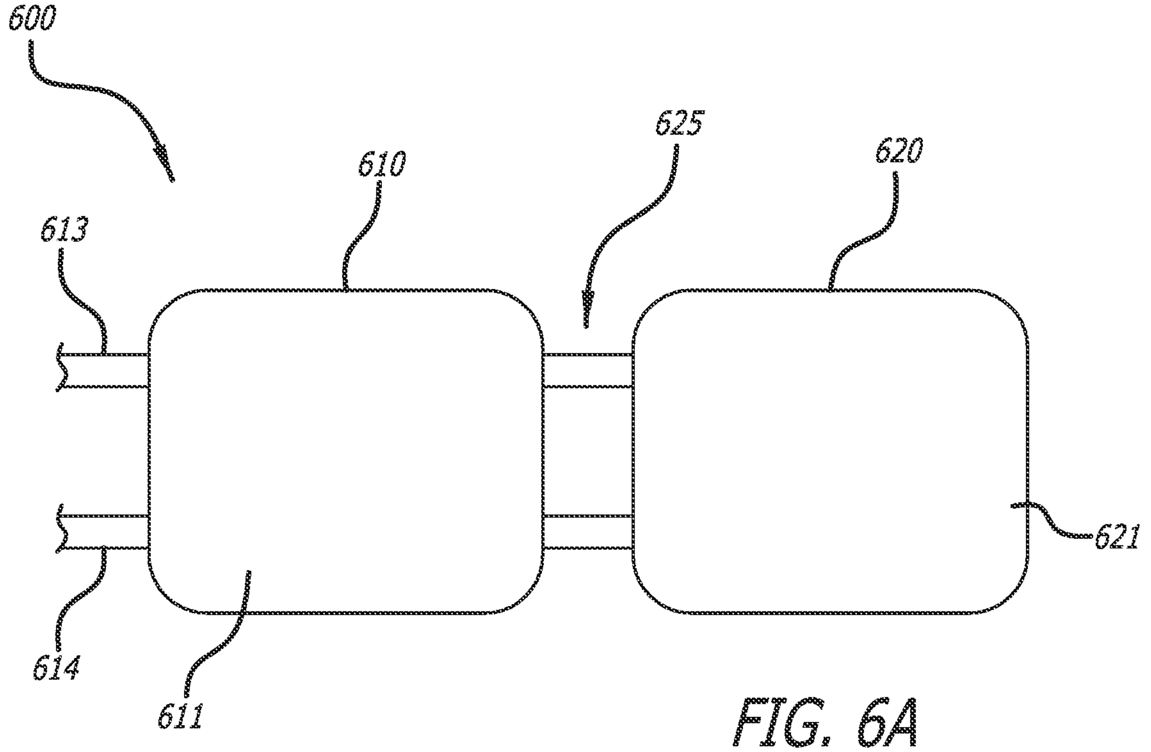
FIG. 6A is an illustration of a thermal pad system including an attachable pad portion, in accordance with some embodiments.
Figure 6B:
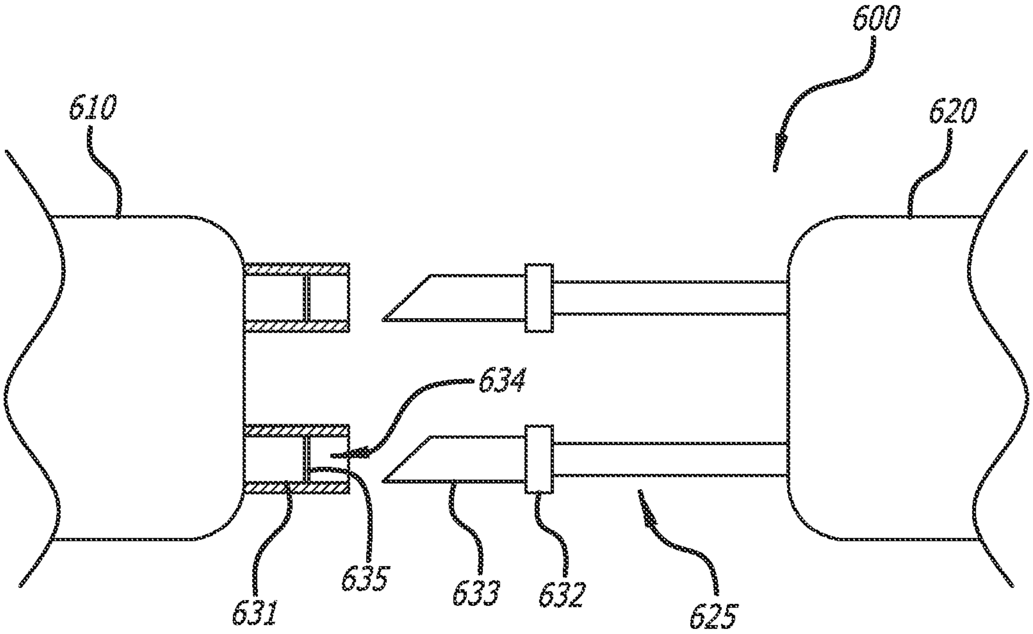
FIG. 6B is a detailed illustration of a coupling portion of the thermal pad system of FIG. 6A, in accordance with some embodiments.

FIGS. 6A-6C illustrate a thermal pad system 600, in accordance with some embodiments. In some instances, a TTM therapy may be better facilitated by adding a second thermal pad to a first pad to increase the patient contact area. FIG. 6A is a top view illustration of the thermal pad system 600. The thermal pad system 600 includes a first pad 610 and a second pad 620 coupleable to the first pad 610 (shown coupled together in FIG. 6A). The first pad 610 includes a fluid inlet 613 and a fluid outlet 614. The first pad 610 defines a first fluid patient contact area 611, and the second pad 620 defines a second patient contact area 621. In use, the clinician may connect the second pad 620 to the first pad 610 to increase the patient contract area. As such, the first patient contact area 611 of the first thermal pad 610 may be combined with the second patient contact area 621 to define a combined patient contact area.

In the illustrated embodiment, the first pad 610 and the second pad 620 define substantially rectangular shapes, so that when coupled together, the patient contact area is extended in one direction. In other embodiments, one or both of the first pad 610 and the second pad 620 may define non-rectangular shapes, so that when coupled together, the patient contact area is extended in more than one direction The thermal pad system 600 includes fluid transfer conduits 625 extending between the first pad 610 and the second pad 620. The fluid conduits 625 may provide for flow of water 120 between the first pad 610 and the second pad 620. In use, the second pad 620 may be coupled with the first pad 610 by the clinician. The fluid transfer conduits 625 may facilitate placement of the second pad 620 adjacent first pad 610 to minimize space between the first pad 610 and the second pad 620. In other embodiments, the fluid conduits 625 may provide for placement of the second pad 620 on the patient at a location spaced away from the first pad 610. For example, the first pad 610 may be placed on a front side of a torso of the patient and the second pad 620 may be placed on a back side of the torso. In such embodiments, the fluid transfer conduits 625 include a sufficient length to extend between the first pad 610 and the second pad 620.

FIG. 6B is a detailed illustration of the fluid conduits 625. The fluid conduits 625 may include a connector set 630. For example, each fluid conduit 625 may include a first connector 631 and a complementary second connector 632. The first connector 631 may be attached to the first pad 610 and the second connector 632 may be attached to the second pad 620. By way of further example, the second connector 632 may include a spike 633 configured for insertion within an opening 634 of the first connector and the first connector 631 may include a septum 635 extending across the opening 634 preventing fluid flow through first connector 631. In use, insertion of the spike 633 may rupture the septum 635. By way of summary, the septums 635 may prevent the flow of water 120 through the first connectors 631 unless the second pad 620 is coupled with the first pad 610, and the spikes 633 rupture the septums 635 allowing the water 120 to flow between the pads 610, 620 when the second pad 620 is coupled with the first pad 610.

In some embodiments, the thermal pad system 600 may include additional thermal pads coupled to each other. The thermal pad system 600 may include 2, 3, 4, 5, or more thermal pads.

Figure 7A:
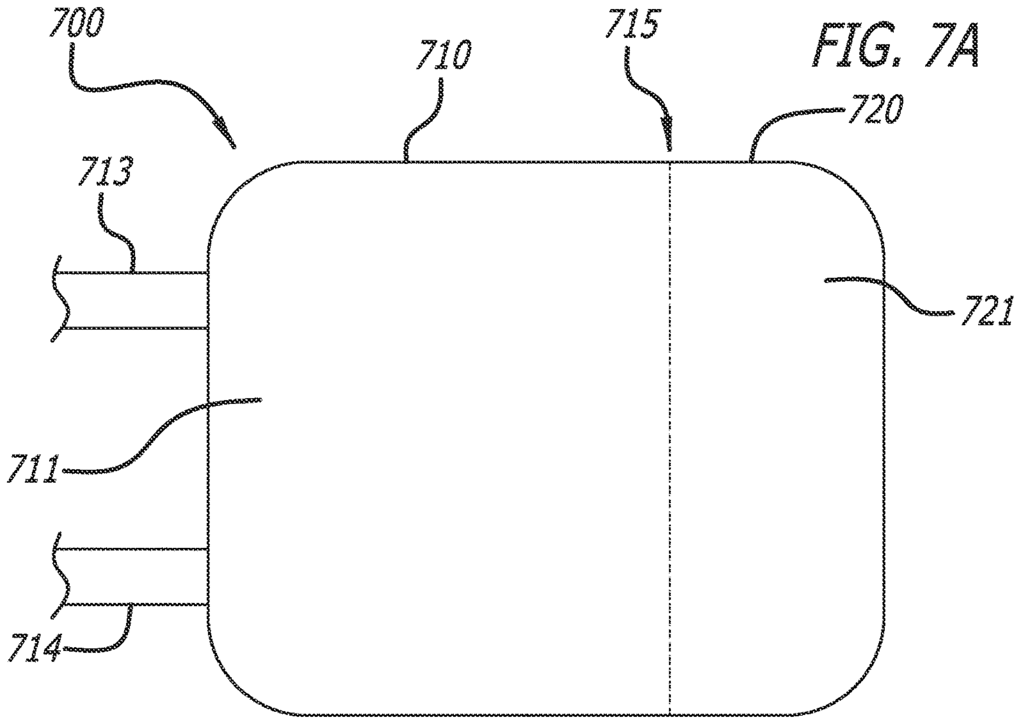
FIG. 7A is an illustration of a thermal pad system including a removable pad portion, in accordance with some embodiments.

FIG. 7A illustrates a top view of a thermal pad 700 having one or more removable pad portions. In some instances, a TTM therapy for a patient may be better facilitated by a thermal pad having a reduced patient contact area, which may reduce patient shivering. The thermal pad 700 comprises a removable portion 720 coupled to a remaining portion 710. The removable portion 720 includes a patient contact area 721 and the remaining portion 710 includes a remaining patient contact area 711. The remaining portion 710 includes a fluid inlet 713 and a fluid outlet 714. The thermal pad 700 is convertible from a first patient contact area to a second patient contact area, wherein the first patient contact area comprises the removable patient contact area 721 combined with the remaining patient contact area 711, and the second patient contact area comprises only the remaining patient contact area 711.

A separation portion 715 is disposed between the removable portion 720 and the remaining portion 710. The separation portion 715 may comprise materials and/or structure to facilitate separation of the removable portion 720 from the remaining portion 710. In some embodiments, the separation portion 715 may include a perforation (not shown). In other embodiments, the removable portion 720 may be coupled to the remaining portion 710 via 1, 2, 3, 4, or more discreet connecting elements (not shown) extending between the remaining portion 710 and the removable portion 720. In some embodiments, the separation portion 715 may facilitate separation of the removable portion 720 from the remaining portion 710 via the use of a tool by the clinician such as a knife or scissors.

As illustrated in FIG. 7A, the removable portion 720 may be coupled to the remaining portion 710 along a partial perimeter of the remaining portion 710. The partial perimeter may extend along a single side of the remaining portion (e.g., a straight side portion of a rectangular shape) or along more than one side including an entire circumference of the remaining portion 710. In some embodiments, the thermal pad 700 may include more than one removable portion 720 and in such embodiments, one removable portion may be coupled with another removable portion.

Figure 7B:
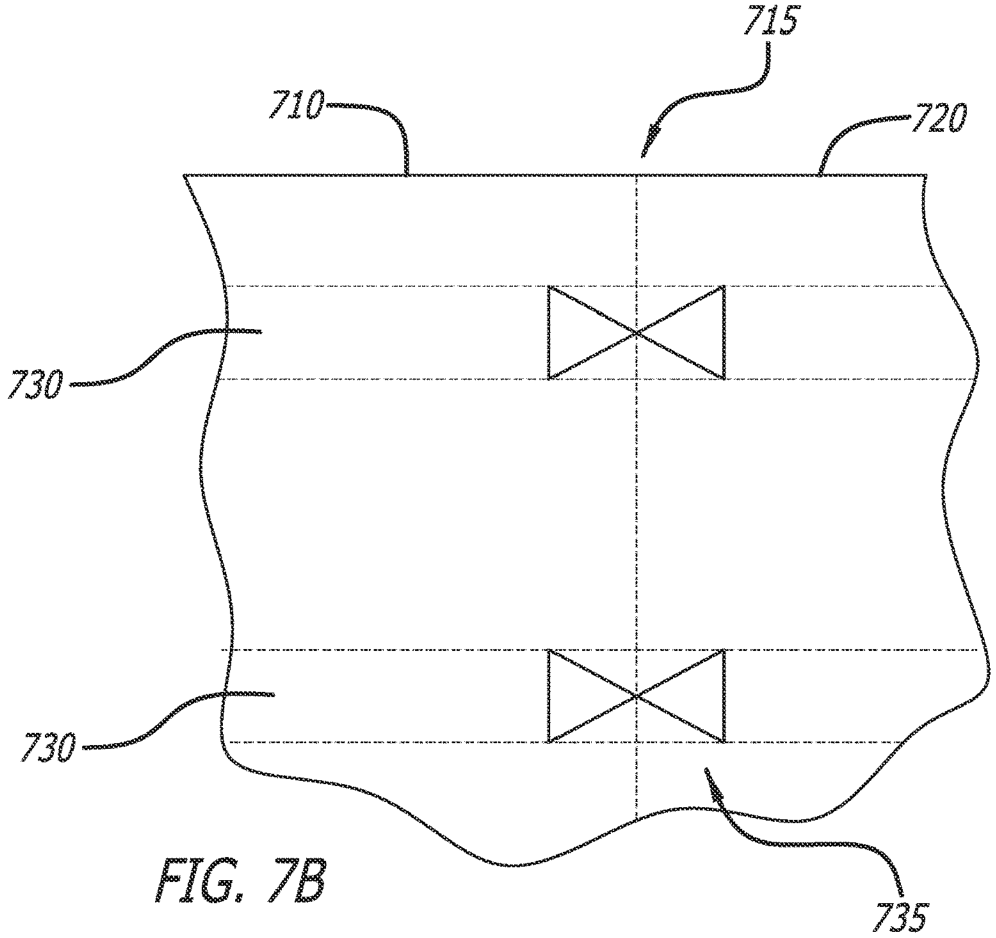
FIG. 7B is a detailed illustration of a separating portion of the thermal pad system of FIG. 7A, in accordance with some embodiments.

FIG. 7B is a detailed illustration of a portion of the thermal pad 700 showing one or more fluid conduits 730 extending across the separation portion 715. The fluid conduits 730 may provide for flow of TTM fluid 112 between the removable portion 720 from the remaining portion 710. Each of the fluid conduits 730 may include one or more occlusion mechanisms 735 configured for occlusion of the fluid conduits 730 of the upon removal of the removable portion 720. The occlusion mechanism 735 may be disposed in an open state (i.e., allowing flow through the fluid conduit 730) when the removable portion 720 is coupled to the remaining portion 710, and the occlusion mechanism 735 may be disposed in a closed state (i.e., occluding the fluid conduit 730) when the removable portion 720 is decoupled from the remaining portion 710.

Figure 7C:
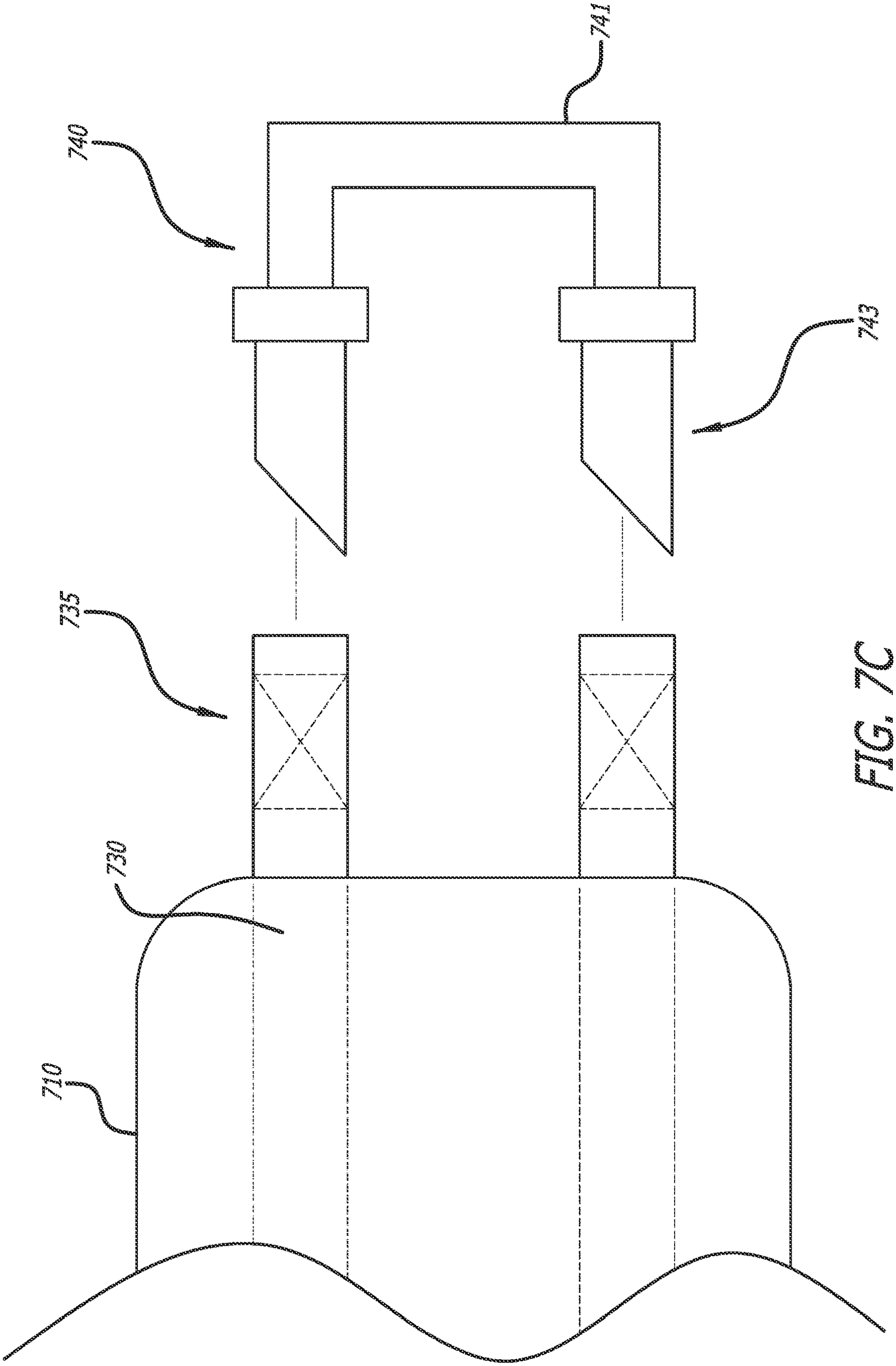
FIG. 7C is an illustration of bypass tube in conjunction with a remaining pad portion of the thermal pad system of FIG. 7A, in accordance with some embodiments.

FIG. 7C is a detailed illustration of a remaining portion 710 showing the fluid conduits 730 extending away from the remaining portion 710 after separation of the removable portion 720. The remaining portion 710 may include the occlusion mechanisms 735 to seal the open ends of the fluid conduits 730. In some embodiments, the occlusion mechanisms 735 may include a bypass conduit 740 including a tubing segment 741 extending between spikes 743 coupled thereto. The spikes 743 are configured for insertion within the open end of the fluid conduits 730 to form a fluid coupling with the fluid conduits 730. In use, water 120 flows out of one fluid conduit 730, through the bypass conduit 740 and into the other fluid conduit 730.

In other embodiments, the occlusion mechanism 735 may comprise a clamp(s) (not shown) configured to occlude the fluid conduits 730. In other embodiments, the occlusion mechanism 735 may comprise a plug(s) (not shown) configured for insertion within the fluid conduits 730 thereby sealing the open end. Other mechanisms, devices, and methods suitable for occluding the open end of each fluid conduit 730, as may be considered by one of ordinary skill, are included in this disclosure.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A medical pad for exchanging thermal energy between a targeted temperature management (TTM) fluid and a patient, the medical pad comprising:
- a fluid channel extending between a fluid inlet positioned at a perimeter edge of the medical pad and a fluid outlet centrally positioned on the medical pad, wherein the fluid channel defines a spiral shape converging radially inward from the fluid inlet toward the fluid outlet, and
- a bottom channel wall disposed between the TTM fluid and the patient during use of the medical pad, the bottom channel wall having an inner surface in contact with the TTM fluid and an outer surface in contact with the patient, the inner surface and the outer surface defining a thickness of the bottom channel wall, wherein:
  - the bottom channel wall (i) is formed of a material having a first thermal conductivity and (ii) includes elements embedded within the bottom channel wall, the elements formed of a material having a second thermal conductivity to define a composite thermal conductivity of the bottom channel wall that is greater than the first thermal conductivity, and
  - thermal energy exchange between the TTM fluid and the patient is defined in accordance with the composite thermal conductivity.

2. The medical pad according to claim 1, wherein the elements include one or more of particles, nano-particles, composites, fibers, fluid pockets, bars extending across the thickness of the bottom channel wall, or layers extending along the bottom channel wall.

3. The medical pad according to claim 1, wherein:
- centrifugal acceleration of a fluid flow within the fluid channel induces turbulence of the fluid flow within the fluid channel,
- the induced turbulence defines a first enhancement of a convection coefficient of the TTM fluid with respect to the bottom channel wall, and
- the thermal energy exchange between the TTM fluid and the patient is defined in accordance with the convection coefficient including the first enhancement.

4. The medical pad according to claim 3, wherein:
- the fluid channel comprises at least one pair of channel walls extending along the fluid channel,
- the at least one pair of channel walls face each other from opposite sides of the fluid channel,
- the fluid channel further comprises a plurality of wall segments extending across at least a majority of the fluid channel,
- a first subset of the plurality of wall segments extends away from one of the at least one pair of channel walls,
- a second subset of the plurality of wall segments extends away from the other of the pair of channel walls, and
- each wall segment of the second subset is disposed between adjacent wall segments of the first subset.

5. The medical pad according to claim 4, wherein:

fluid flow between the plurality of wall segments induces turbulence of the fluid flow within the fluid channel, the induced turbulence defines a second enhancement of the convection coefficient of the TTM fluid with respect to the bottom channel wall, and the thermal energy exchange between the TTM fluid and the patient is defined in accordance with the convection coefficient including the second enhancement.

6. The medical pad according to claim 1, wherein:

the fluid channel comprises a plurality of inward protruding ribs disposed along one or more walls of the fluid channel, the plurality of inward protruding ribs are disposed at an angle with respect to the fluid channel, the plurality of inward protruding ribs induce a swirling turbulence of a fluid flow along the fluid channel, the swirling turbulence defines a third enhancement of a convection coefficient of the TTM fluid with respect to the bottom channel wall, and the thermal energy exchange between the TTM fluid and the patient is defined in accordance with the convection coefficient including the third enhancement.

7. The medical pad according to claim 1, further comprising:

a first pad portion defining a first patient contact area; and a separate second pad portion defining a second patient contact area, wherein the separate second pad portion is directly coupleable with the first pad portion to define a combined patient contact area equaling a sum of the first patient contact area and the second patient contact area.

8. The medical pad according to claim 1, wherein a patient contact area of the medical pad includes:

a first patient contact area defined by a first pad portion; and a second patient area defined by a second pad portion, wherein the second pad portion is separable from the first pad portion to define a reduced patient contact area equaling the first patient contact area.

9. A method of providing a targeted temperature management (TTM) therapy to a patient, comprising:

applying a thermal contact pad to the patient, altering a patient contact area of the thermal contact pad to accommodate a size of the patient, establishing a flow of TTM fluid through the thermal contact pad by directing TTM fluid flow along a fluid channel to enhance a heat transfer convection coefficient of the thermal contact pad, wherein the fluid channel defines a spiral shape converging radially inward from a fluid inlet positioned at a perimeter edge of the thermal contact pad toward a fluid outlet centrally positioned on the thermal contact pad; and exchanging thermal energy with the patient through a bottom wall of the thermal contact pad, wherein:

the bottom wall is disposed between the TTM fluid and the patient during use of the thermal contact pad, the bottom wall has an inner surface in contact with the TTM fluid and an outer surface in contact with the patient, and the bottom wall comprises embedded elements configured to enhance a thermal conductivity of the bottom wall.

10. The method according to claim 9, wherein altering the patient contact area comprises coupling a second thermal contact pad to the thermal contact pad to increase the patient contact area.

11. The method according to claim 9, wherein altering the patient contact area comprises removing a separable portion of the thermal contact pad from the thermal contact pad to decrease the patient contact area to an area defined by a remaining portion of the thermal contact pad.

12. The method according to claim 9, wherein:

the fluid channel comprises at least one pair of channel walls extending along the fluid channel, the channel walls face each other from opposite sides of the fluid channel, the fluid channel further comprises a plurality of wall segments extending across at least a majority of the fluid channel, a first subset of the plurality of wall segments extends away from one of the at least one pair of channel walls, a second subset of the plurality of wall segments extends away from the other a second of the at least one pair of channel walls, and each wall segment of the second subset is disposed between adjacent wall segments of the first subset.

13. A medical pad for exchanging thermal energy between a targeted temperature management (TTM) fluid and a patient, the medical pad comprising:

a fluid channel extending between a fluid inlet and a fluid outlet, wherein:

the fluid channel defines a double spiral shape comprising:

a first channel portion converging radially inward from the fluid inlet disposed at a perimeter edge of the medical pad toward a central location;

a second channel portion expanding radially outward from the central location toward an outlet disposed at the perimeter edge of the medical pad; and a fluid connection at the central location between the first channel portion and the second channel portion, and the second channel portion is disposed between adjacent wraps of the first channel portion; and a bottom channel wall disposed between the TTM fluid and the patient during use of the medical pad, the bottom channel wall having an inner surface in contact with the TTM fluid and an outer surface in contact with the patient, the inner surface and the outer surface defining a thickness of the bottom channel wall, wherein:

the bottom channel wall (i) is formed of a material having a first thermal conductivity and (ii) includes elements embedded within the bottom channel wall, the elements formed of a material having a second thermal conductivity to define a composite thermal conductivity of the bottom channel wall that is greater than the first thermal conductivity, and thermal energy exchange between the TTM fluid and the patient is defined in accordance with the composite thermal conductivity.

14. The medical pad according to claim 13, wherein a fluid flow in the first channel portion and the second channel portion is in opposite directions.

15. The medical pad according to claim 13, wherein:

centrifugal acceleration of a fluid flow within the fluid channel induces turbulence of the fluid flow within the fluid channel, the induced turbulence defines a first enhancement of a convection coefficient of the TTM fluid with respect to the bottom channel wall, and the thermal energy exchange between the TTM fluid and the patient is defined in accordance with the convection coefficient including the first enhancement.

16. The medical pad according to claim 13, wherein:

the fluid channel comprises at least one pair of channel walls extending along the fluid channel, the channel walls face each other from opposite sides of the fluid channel, the fluid channel further comprises a plurality of wall segments extending across at least a majority of the fluid channel, a first subset of the plurality of wall segments extends away from one of the at least one pair of channel walls, a second subset of the plurality of wall segments extends away from the other a second of the at least one pair of channel walls, and each wall segment of the second subset is disposed between adjacent wall segments of the first subset.

17. The medical pad according to claim 16, wherein:

fluid flow between the plurality of wall segments induces turbulence of the fluid flow within the fluid channel, the induced turbulence defines a second enhancement of a convection coefficient of the TTM fluid with respect to the bottom channel wall, and the thermal energy exchange between the TTM fluid and the patient is defined in accordance with the convection coefficient including the second enhancement.

18. The medical pad according to claim 13, wherein:

the fluid channel comprises a plurality of inward protruding ribs disposed along one or more walls of the fluid channel, the plurality of inward protruding ribs are disposed at an angle with respect to the fluid channel, the plurality of inward protruding ribs induce a swirling turbulence of a fluid flow along the fluid channel, the swirling turbulence defines a third enhancement of a convection coefficient of the TTM fluid with respect to the bottom channel wall, and the thermal energy exchange between the TTM fluid and the patient is defined in accordance with the convection coefficient including the third enhancement.

19. The medical pad according to claim 13, further comprising:

a first pad portion defining a first patient contact area; and a separate second pad portion defining a second patient contact area, wherein the second separate pad portion is directly coupleable with the first pad portion to define a combined patient contact area equaling a sum of the first patient contact area and the second patient contact area.

20. The medical pad according to claim 13, wherein a patient contact area of the medical pad includes:

a first patient contact area defined by a first pad portion; and a second patient area defined by a second pad portion, wherein the second pad portion is separable from the first pad portion to define a reduced patient contact area equaling the first patient contact area.

* * * * *